United States Patent

Gilbert et al.

Patent Number: 5,693,643
Date of Patent: Dec. 2, 1997

[54] HYDANTOIN AND SUCCINIMIDE-SUBSTITUTED DERIVATIVES OF SPIROINDANYLCAMPHORSULFONYL OXYTOCIN ANTAGONISTS

[75] Inventors: Kevin Gilbert, Bechtelsville; Peter D. Williams, Harleysville; Ben E. Evans; Doug W. Hobbs, both of Lansdale; Daniel F. Veber, Ambler, all of Pa.

[73] Assignee: Merck & Co., Inc., Rahway, N.J.

[21] Appl. No.: 464,808

[22] PCT Filed: Dec. 23, 1993

[86] PCT No.: PCT/US93/12565

§ 371 Date: Aug. 15, 1995

§ 102(e) Date: Aug. 15, 1995

[87] PCT Pub. No.: WO94/14438

PCT Pub. Date: Jul. 7, 1994

Related U.S. Application Data

[63] Continuation-in-part of Ser. No. 993,861, Dec. 23, 1992, abandoned, which is a continuation-in-part of Ser. No. 760,416, Sep. 16, 1991, abandoned.

[51] Int. Cl.$^6$ .................. A61K 31/445; A61K 31/40; C07D 241/04; C07D 401/08
[52] U.S. Cl. .................. 514/253; 514/255; 514/278; 514/397; 514/409; 544/230; 544/360; 544/366; 544/372; 546/17
[58] Field of Search .................. 514/253, 255, 514/278, 397, 409; 544/230, 360, 366, 372; 546/17

[56] References Cited

U.S. PATENT DOCUMENTS

| | | | |
|---|---|---|---|
| 3,301,857 | 1/1967 | Berger et al. | 260/288 |
| 3,654,287 | 4/1972 | Dykstra et al. | 260/293.62 |
| 3,666,764 | 5/1972 | Campbell et al. | 260/293.62 |
| 4,379,933 | 4/1983 | Ong et al. | 546/17 |
| 5,091,387 | 2/1992 | Evans et al. | 514/278 |
| 5,204,349 | 4/1993 | Bock et al. | 514/253 |

FOREIGN PATENT DOCUMENTS

| | | |
|---|---|---|
| 0 444 945 | 9/1991 | European Pat. Off. |
| 445974 | 9/1991 | European Pat. Off. |
| 0 450 761 A1 | 10/1991 | European Pat. Off. |
| 0 486 280 A2 | 5/1992 | European Pat. Off. |
| 1335831 | 8/1963 | France. |
| 2718455 | 1/1967 | Germany. |
| 2458176 | 6/1975 | Germany. |
| 2458177 | 9/1976 | Germany. |
| 2636735 | 3/1977 | Germany. |

OTHER PUBLICATIONS

J. Med. Chem., Evans et al., Orally Active, Nonpeptide Oxytocin Antagonists, 1992, vol. 35, pp. 3919–3927.
J. Med. Chem., Evans et al., Nanomolar–Affinity, Non–Peptide Oxytocin Receptor Antagonists, 1993, vol. 36, pp. 3993–4005.
J. Pharm. Sci (1982) 71, 3 pp. 291–294, Crooks et al.
Heterocycles (1984) 22, 2, pp. 311–331, Laus et al.
J. Org. Chem. (1971) 36, 5, pp. 650–654, Matier, et al.
J. Org. chem. (1976) 41, 15, pp. 2628–2633, Parkham et al.

Primary Examiner—Ba K. Trinh
Attorney, Agent, or Firm—William H. Nicholson; Mary A. Appollina

[57] ABSTRACT

Compounds of formula (I) wherein X is (a) or (b), R is Het as defined in the description. These compounds are oxytocin and vasopressin antagonists useful in the treatment of preterm labor, dysmenorrhea, and for the stoppage of labor preparatory to Cesarean delivery.

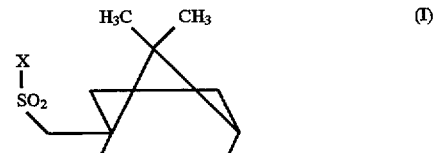

(I)

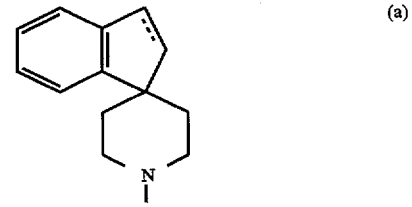

(a)

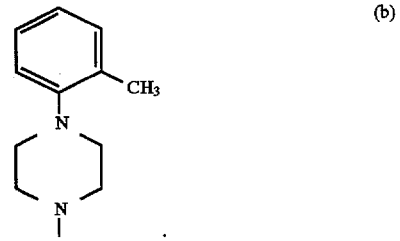

(b)

16 Claims, No Drawings

HYDANTOIN AND SUCCINIMIDE-SUBSTITUTED DERIVATIVES OF SPIROINDANYLCAMPHORSULFONYL OXYTOCIN ANTAGONISTS

FIELD OF THE INVENTION

This application is a 371 of PCT/US 93/12565, filed Dec. 23, 1993 which is a continuation-in-part of application Ser. No. 07/993,861, filed Dec. 23, 1992 now abandoned, which is a continuation-in-part of application Ser. No. 07/760,416, filed Sep. 16, 1991, now abandoned.

The present invention provides novel compounds, novel compositions, methods of their use and methods of their manufacture, such compounds generally pharmacologically useful as agents in obstetric and gynecologic therapy. The aforementioned pharmacologic activities are useful in the treatment of mammals. More specifically, the compounds of the present invention can be used in the treatment of preterm labor, stopping labor preparatory to Cesarean delivery, and in the treatment of dysmenorrhea. At the present time, there is a need in the area of obstetric and gynecologic therapy for such agents.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include $\beta_2$-adrenergic agonists, magnesium sulfate and ethanol. Ritodrine, the leading $\beta_2$-adrenergic agonist, causes a number of cardiovascular and metabolic side effects in the mother, including tachycardia, increased renin secretion, hyperglycemia (and reactive hypoglycemia in the infant). Other $\beta_2$-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

It has been proposed that a selective oxytocin antagonist would be the ideal tocolytic agent. In the last few years, evidence has accumulated to strongly suggest that the hormone oxytocin is the physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part as a result of a well-documented increase in the number of oxytocin receptors in this tissue. This "up-regulation" of oxytocin receptors and enhanced uterine sensitivity appears to be due to trophic effects of rising plasma levels of estrogen towards term. By blocking oxytocin, one would block both the direct (contractile) and indirect (enhanced prostaglandin synthesis) effects of oxytocin on the uterus. A selective oxytocin blocker, or antagonist, would likely be more efficacious for treating preterm labor than current regimens. In addition, since oxytocin at term has major effects only on the uterus, such an oxytocin antagonizing compound would be expected to have few, if any, side effects.

The compounds of the present invention can also be useful in the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, a selective oxytocin antagonist can be more efficacious for treating dysmenorrhea then current regimens.

It is, therefore, a purpose of this invention to provide substances which more effectively antagonize the function of oxytocin in disease states in animals, preferably mammals, especially in humans. It is another purpose of this invention to prepare novel compounds which more selectively inhibit oxytocin. It is still another purpose of this invention to provide a method of antagonizing the functions of oxytocin when oxytocin activity is responsible for causing disease states in mammals. It is also a purpose of this invention to develop a method of preventing or treating oxytocin-related disorders of preterm labor and dysmenorrhea by antagonizing oxytocin.

It has now been found that compounds of the present invention are antagonists of oxytocin and bind to the oxytocin receptor. When the oxytocin receptor is bound by the compounds of the present invention, oxytocin is antagonized by being blocked from its receptor and thus being unable to exert its biologic or pharmacologic effects. These compounds are useful in the treatment and prevention of oxytocin-related disorders of animals, preferably mammals and especially humans. These disorders are primarily preterm labor and dysmenorrhea. The compounds would also find usefulness for stoppage of labor preparatory to Cesarean delivery.

SUMMARY OF THE INVENTION

The compounds of the present invention and their pharmaceutically acceptable salts and esters are those of the general structural formula:

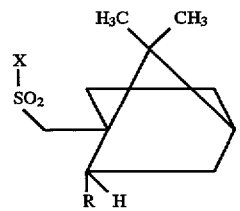

wherein

X is

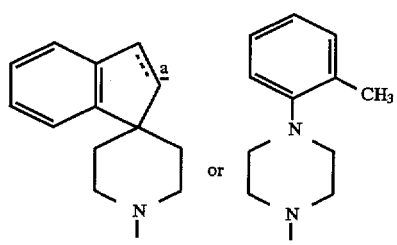 or 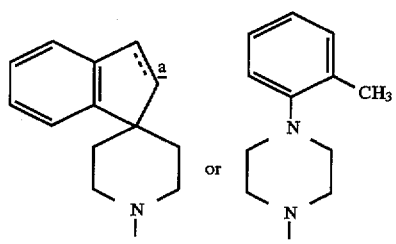

a is a single or double bond,

R is Het, wherein

Het is a substituted saturated or unsaturated heterocyclic ring wherein said substituents are independently one or more of $R^1$, $R^2$, $R^3$, Alk-$R^1$, Alk-$R^2$, Alk-$R^3$, —NHC(O)—Alk-$R^2R^3$, —$NR^5$—Alk-$R^2R^3$ or Alk-$R^2R^3$; where Alk is $C_{1-10}$ alkyl and $R^1$, $R^2$ and $R^3$ are independently selected from the group consisting of hydrogen, halogen, $C_{2-10}$ alkenyl, methylene, $C_{1-10}$ alkoxycarbonyl, $C_{1-10}$ alkoxycarbonyl-$C_{1-10}$ alkylamino, $C_{1-10}$ alkoxycarbonylamino, $C_{1-10}$ alkylamino-$C_{1-10}$ alkylaminocarbonyl, $C_{1-10}$ alkylcarbonylamino, —S—$R^4$, $C_{1-10}$ alkylcarbonyloxy, $C_{1-10}$ alkylsulfonyl, $C_{1-10}$ alkylthio, amino, amino $C_{1-10}$ alkylcarbonylamino, amino $C_{1-10}$ alkylamino, carbonylamino, carbamoyl, carboxyl $C_{1-10}$ alkylamino, carboxyl, cyano, di-$C_{1-10}$ alkylamino, di-$C_{1-10}$ alkylamino-$C_{1-10}$ alkylamino, di-$C_{1-10}$ alkylamino-$C_{1-10}$ alkylthio, di-$C_{1-10}$ alkylamino-$C_{1-10}$ alkylaminocarbonyl, guanidinyl, hydroxyl, hydroxyl $C_{1-10}$ alkylamino, imidazolyl, imidazolyl amino, imidazolyl $C_{1-10}$ alkylamino, imidazolyl $C_{1-10}$ alkylaminocarbonyl, morpholinyl, thiomorpholinyl, dioxothiomorpholinyl, indolyl, oxo, oxiranyl, phenyl, piperidinylamino, piperazinyl, pyrrolidinyl, sulfonyl, tetrazolyl $C_{1-10}$ alkylcarbonylamino, tetrazolylaminocarbonyl, phosphoryl, phosphoryl $C_{1-10}$ alkylamino and thiono;

$R^4$ is selected from the group consisting of imidazolyl, $C_{1-10}$ alkoxycarbonyl-$C_{1-10}$ alkyl, di-$C_{1-10}$ alkylamino-$C_{1-10}$ alkyl and $C_{1-5}$ alkyl; and $R^5$ is selected from the group consisting of hydrogen and $C_{1-5}$ alkyl.

In one embodiment of the instant invention are compounds represented by the formula

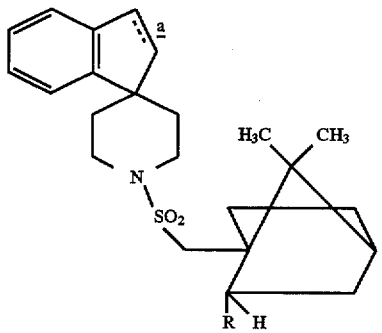

wherein a is a single or double bond,

R is Het, wherein

Het is a mono, di, tri or tetra substituted saturated or unsaturated 5 or 6 membered heterocyclic or 7 to 10 membered heterobicyclic ring containing 1, 2 or 3 nitrogen atoms, wherein said substituents are independently one or more of $R^1$, $R^2$, $R^3$, Alk-$R^1$, Alk-$R^2$, Alk-$R^3$, —NHC(O)—Alk—$R^2R^3$, —$NR^5$—Alk—$R^2R^3$ or Alk—$R^2R^3$; where Alk is $C_{1-10}$ alkyl and $R^1$, $R^2$ and $R^3$ are independently selected from the group consisting of hydrogen, halogen, $C_{2-10}$ alkenyl, methylene, $C_{1-10}$ alkoxycarbonyl, $C_{1-10}$ alkoxycarbonyl-$C_{1-10}$ alkylamino, $C_{1-10}$ alkylcarbonylamino, $C_{1-10}$ alkylsulfonyl, —S—$R^4$, amino, amino-$C_{1-10}$ alkylcarbonylamino, amino $C_{1-10}$ alkylamino, carbamoyl, carboxyl $C_{1-10}$ alkylamino, carboxyl, cyano, di-$C_{1-10}$ alkylamino, di-$C_{1-10}$ alkylamino-$C_{1-10}$ alkylamino, di-$C_{1-10}$ alkylamino-$C_{1-10}$ alkylthio, di-$C_{1-10}$ alkylamino-$C_{1-10}$ alkylaminocarbonyl, guanidinyl, hydroxyl, hydroxyl-$C_{1-10}$ alkylamino, imidazolyl, imidazolyl amino, imidazolyl-$C_{1-10}$ alkylamino, morpholinyl, thiomorpholinyl, dioxothiomorpholinyl, indolyl, oxo, oxiranyl, phenyl, piperidinylamino, piperazinyl, sulfonyl, phosphoryl, phosphoryl $C_{1-10}$ alkylamino and thiono;

$R^4$ is selected from the group consisting of imidazolyl, $C_{1-10}$ alkoxycarbonyl-$C_{1-10}$ alkyl, di-$C_{1-10}$ alkylamino-$C_{1-10}$ alkyl and $C_{1-5}$ alkyl; and $R^5$ is selected from the group consisting of hydrogen and $C_{1-5}$ alkyl.

In a second embodiment of the instant invention are compounds represented by the formula or a pharmaceutically acceptable salt thereof, wherein a is a single or double bond, R is Het, wherein Het is a mono, di, tri or tetra substituted saturated or unsaturated 5 or 6 membered heterocyclic ring containing 1, or 2 nitrogen atoms that is bonded to said bicyclic ring at one of said heterocyclic ring's nitrogen atoms, wherein said substituents are independently one or more of $R^1$, $R^2$, $R^3$, Alk-$R^1$, Alk-$R^2$, Alk-$R^3$ or Alk-$R^2R^3$; and where Alk is $C_{1-10}$ alkyl and $R^1$, $R^2$ and $R^3$ are independently selected from the group consisting of hydrogen, $C_{2-10}$ alkenyl, $C_{1-10}$ alkoxycarbonyl, $C_{1-10}$ alkoxycarbonyl-$C_{1-10}$ alkylamino, $C_{1-10}$ alkoxycarbonylamino, $C_{1-10}$ alkylamino-$C_{1-10}$ alkylaminocarbonyl, $C_{1-10}$ alkylcarbonylamino, $C_{1-10}$ alkylcarbonyloxy, $C_{1-10}$ alkylsulfonyl, $C_{1-10}$ alkylthio, amino, amino-$C_{1-10}$ alkylcarbonylamino, carbonylamino, carboxyl $C_{1-10}$ alkylamino, carboxyl, carboxyl $C_{1-10}$ alkylamino, cyano, di-$C_{1-10}$ alkylamino, di-$C_{1-10}$ alkylamino-$C_{1-10}$ alkylaminocarbonyl, guanidinyl, hydroxyl, imidazolyl, imidazolyl $C_{1-10}$ alkylaminocarbonyl, indolyl, oxo, phenyl, piperidinylamino, piperizinyl, pyrrolidinyl, sulfonyl, tetrazolyl-$C_{1-10}$ alkylcarbonylamino, tetrazolylaminocarbonyl and thiono.

Salts encompassed within the term "pharmaceutically acceptable salts" refer to non-toxic salts of the compounds of this invention which are generally prepared by reacting the free base with a suitable organic or inorganic acid. Representative salts include the following salts:

| | |
|---|---|
| Acetate | Lactobionate |
| Benzenesulfonate | Laurate |
| Benzoate | Malate |
| Bicarbonate | Maleate |
| Bisulfate | Mandelate |
| Bitartrate | Mesylate |
| Borate | Methylbromide |
| Bromide | Methylnitrate |
| Calcium Edetate | Methylsulfate |
| Camsylate | Mucate |
| Carbonate | Napsylate |
| Chloride | Nitrate |
| Clavulanate | N-methylglucamine |
| Citrate | Oxalate |
| Dihydrochloride | Pamoate (Embonate) |
| Edetate | Palmitate |
| Edisylate | Pantothenate |
| Estolate | Phosphate/diphosphate |
| Esylate | Polygalacturonate |
| Fumarate | Salicylate |
| Gluceptate | Stearate |
| Gluconate | Subacetate |
| Glutamate | Succinate |
| Glycollylarsanilate | Tannate |
| Hexylresorcinate | Tartrate |
| Hydrabamine | Teoclate |
| Hydrobromide | Tosylate |
| Hydrocloride | Triethiodide |
| Hydroxynaphthoate | Valerate |
| Iodide | |
| Isethionate | |
| Lactate | |

The term "pharmacologically effective amount" shall mean that amount of a drug or pharmaceutical agent that will elicit the biological or medical response of a tissue, system, animal or human that is being sought by a researcher or clinician.

The term "alkyl" shall mean straight or branched chain alkanes of one to ten total carbon atoms or any number within this range.

The term "alkenyl" shall mean straight or branched chain alkenes, with one or more degrees of unsaturation at any position on the chain, of two to ten total carbon atoms, or any number within this range.

The term "aryl" shall mean phenyl.

The term "cycloalkyl" shall mean cyclic rings of alkanes, alkenes or alkynes with one or more degrees of unsaturation at any position of the ring, of three to eight total carbon atoms.

Whenever the terms "alkyl" or "aryl" or either of their prefix roots appear in a name of a substituent (e.g., aralkoxyaryloxy) they shall be interpreted as including those limitations given above for "alkyl" and "aryl". Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The term "heterocyclic" or "heterocycle," as used herein except where noted, represents a stable mono, di, tri or tetra-substituted 5- to 7-membered mono- or bicyclic or stable mono, di, tri or tetra-substituted 7- to 10-membered bicyclic heterocyclic ring system any ring of which may be saturated or unsaturated, and which consists of carbon atoms and from one to three heteroatoms selected from the group consisting of N and O. The heterocyclic ring may be attached at any heteroatom or carbon atom which results in the creation of a stable structure. Examples of such heterocyclic elements include piperidinyl, piperazinyl, azepinyl, pyrrolyl, dihydropyrrolyl, pyrrolidinyl, pyrazolyl, pyrazolidinyl, 4-piperidonyl, imidizolyl, imidazolinyl, imidazolidinyl, triazolyl, triazolinyl, triazolidinyl, morpholinyl, pyridyl, pyrazinyl, pyrimidinyl, pyridazinyl, oxazolyl, oxazolidinyl, isoxazolyl, isoxazolidinyl, quinuclidinyl, indolyl, quinolinyl, isoquinolinyl, benzimidazolyl, benzopyranyl, benzoxazolyl, oxadiazolyl, triazaspirodecane, pyrrolo-isoxazole, pyrrolo-pyrazole, and pyrrolo-pyrrole.

The term "oxo" shall refer to the substituent =O.

The term "thiono" shall refer to the substituent =S.

The term "phosphoryl" shall refer to the substitutent —OPO(OH)$_2$.

The term "oxiranyl" shall refer to the substituent

The term "dioxothiomorpholinyl" shall refer to the substituent

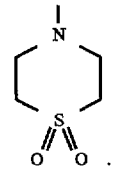

The term "halogen" shall include iodine, bromine, chlorine and fluorine.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "cesarean delivery" shall mean incision through the abdominal and uterine walls for delivery of a fetus.

The term "substituted" shall be deemed to include multiple degrees of substitution by a named substitutent.

The ability of the compounds of the present invention to antagonize oxytocin makes these compounds useful as pharmacologic agents for mammals, especially for humans, for the treatment and prevention of disorders wherein oxytocin may be involved. Examples of such disorders include preterm labor and especially dysmenorrhea. These compounds may also find usefulness for stoppage of labor preparatory to Cesarean delivery.

Because of the known relationship of vasopressin to oxytocin, the compounds of the present invention are also useful as vasopressin antagonists. Vasopressin antagonists are useful in the treatment or prevention of disease states involving vasopressin disorders, including their use as diuretics and their use in congestive heart failure.

The compounds of the present invention can be administered in such oral dosage forms as tablets, capsules (each including timed release and sustained release formulations), pills, powders, granules, elixirs, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.3–6.0 gm/day orally. Intravenously, the most preferred doses will range from 0.1 to about 10 mg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carders to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The compounds of the present invention can be prepared readily according to the following reaction Schemes (in which all variables are as defined before) and Examples or modifications thereof using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Abbreviations used in the Examples are as follows:

TEA=triethylamine

DIEA=diisopropylethylamine

BOP=benzotriazolyloxytris(dimethylamino) phosphonium hexafluorophosphate

THF=tetrahydrofuran

DMF=dimethylformamide

LAH=lithium aluminum hydride

TFA=trifluoroacetic acid

HPLC Method A =15 min. linear gradient 95:5 A:B to 0:100 A:B $A=H_2O$ containing 0.1% by vol. TFA $B=CH_3CN$ containing 0.1% by vol. TFA 2.0 mL/min flow rate 12 cm $C_{18}$ reverse phase column UV detection (215 nm)

HPLC Method B=20 min. linear gradient 90:10 A:B to 5:95 A:B $A=H_2O$ containing 0.1% by vol. phosphoric acid $B=CH_3CN$ containing 0.1% by vol. phosphoric acid

EXAMPLE A

Endo-(1S)-1'-(((2-amino-7,7-dimethylbicyclo(2.2.1)-hept-1-yl)-methyl)-sulfonyl)spiro(1H-indan-1,4'-piperidine)

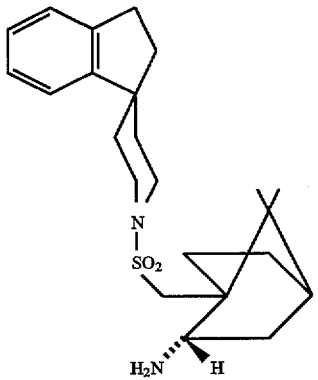

Di-t-butyl dicarbonate (31 g, 0.14 mole available from Aldrich) and bis(2-chloroethyl) amine hydrochloride (21.6 g, 0.12 mole Aldrich) were combined in CH₂Cl₂ (250 ml) stirred at ambient temperature and treated with triethylamine (12.8 g, 0.127 mole) added dropwise over 15 minutes. After 1 hour, another 1.5 ml of triethylamine was added. After a total of 2.5 hours, the mixture was poured onto a silica gel column packed with CH₂Cl₂:hexane (1:1), and eluted with CH₂Cl₂. The combined product fractions were evaporated to dryness in vacuo to give N,N-bis(2-chloroethyl)-t-butyl-carbamate.

To a solution of indene (10.3 g, 89 mmole) in dry tetrahydrofuran (THF, 18 ml) cooled in an ice bath and maintained under a nitrogen blanket was added lithium bis(trimethylsilyl)amide (Aldrich, 177 ml of a 1.0M solution in THF; 177 mmole) over 15 minutes. The mixture was stirred in the cold for 30 minutes, then added over 15 minutes to a solution of N,N-bis(2-chloroethyl)-t-butylcarbamate (21.2 g, 88 mmole) stirred in an ice bath. The mixture was stirred for 2 hours in the cold and for 30 minutes at ambient temperature under nitrogen, then evaporated in vacuo to a foam. CH₂Cl₂ was added and the resulting mixture poured onto a silica gel column packed with 40% hexane in CH₂Cl₂. The column was eluted with 40% hexane in CH₂Cl₂ followed by CH₂CL₂, and the product fractions were evaporated to dryness in vacuo to provide 1'-(t-butyloxycarbonyl)-spiro(indene-1,4'-piperidine).

1'-(t-Butyloxycarbonyl)spiro(indene-1,4'-piperidine) (16 g, 56 mmole) in ethyl acetate (250 ml) was stirred in an ice bath and saturated with HCl(g) for 30 minutes. The mixture was evaporated to dryness. Ethyl acetate was added and removed in vacuo three times, and the residue was triturated with diethyl ether and filtered to provide spiro(1H-indene-1,4'-piperidine) hydrochloride. The free base was obtained by slurrying the hydrochloride in aqueous sodium bicarbonate solution and extracting with CH₂Cl₂. The organic layer was separated, dried over sodium sulfate, filtered, and evaporated to dryness in vacuo to provide spiro(1H-indene-1,4'piperidine.

Spiro(1H-indene-1,4'piperidine) (308 mg, 1.66 mmol) and (+)-10-camphorsulfonyl chloride (418 mg, 1.66 mmol) were combined in CH₂Cl₂ and treated with triethylamine (0.23 ml). The mixture was stirred at ambient temperature for 15 minutes, then poured onto a silica gel column and eluted with 1:1 CH₂Cl₂:hexane. The product fractions were combined and evaporated to dryness in vacuo to provide (1S)-1'-(((7,7-dimethyl-2-oxobicicylo-(2.2.1)hept-1-yl) methyl)sulfonyl)spiro(1H-indene-1,4'-piperidine) as a solid which was recrystallized from petroleum ether and dried overnight in vacuo at ambient temperature.

(1S)-1'-(((7,7-dimethyl-2-oxobicyclo(2.2.1) hept-1-yl) methyl)sulfonyl)spiro(1H-indene-1,4'-piperidine) (30 g, 0.075 mole) in pyridine (500 mL) was heated in an oil bath to 70° C. (internal). Hydroxylamine hydrochloride (30 g) was added in three portions over ca. 20 minutes. After 2 hours, an additional 10 g of hydroxylamine hydrochloride was added (over 10 minutes). At 30, 40, and 50 minutes additional elapsed time, further 3 g lots of hydroxylamine hydrochloride were added. After another 30 minutes, the mixture was poured into water (2 L) and extracted 3 times with ethyl acetate (300 mL portions). The organic layers were combined, washed with 1N HCl (600 mL total), dried over sodium sulfate, filtered, and evaporated to dryness in vacuo. EtOH (abs; ca. 250 mL) was added to the resulting thick syrup and the solution allowed to stand at ambient temperature overnight. The mixture was filtered and the filtrate boiled down to ca. 80 mL. After standing, the mixture was again filtered and boiled down to ca. 20 mL. After a third filtration, the filtered solids were combined to give (1S)-1'-(((7,7-dimethyl-2-oximinobicyclo(2.2.1)hept-1-yl)-methyl) sulfonyl)spiro(1H-indene-1,4'-piperidine) (28 g).

Freshly prepared, activated Raney Nickel catalyst (ca. 30 g) in water was allowed to settle and the water decanted. Abs. ethanol (300 mL) was added, and the mixture swirled and again allowed to settle. The solvent was decanted. Two more wash-decant cycles with 150 mL of ethanol were similarly carried out. (1S)-1'-(((7,7-dimethyl-2-oximinobicyclo (2.2.1)hept-1-yl)methyl)sulfonyl)-spiro (1H-indene-1, 4'-piperidine) (30 g) was stirred in a mixture of abs. ethanol (450 mL) and 2-methoxyethanol (900 mL), nitrogen was bubbled through the suspension/solution, and the Raney Nickel catalyst was added. The mixture was hydrogenated under 50 psi overnight. TLC (9:1 CH₂C₂ MeOH, silica gel) showed the reaction to be complete. The catalyst was removed by filtration, and the filtrate evaporated to dryness in vacuo. The crude solid (27 g) was divided into 7 g batches, and each batch was dissolved in methylene chloride (ca. 200 mL) and flash chromatographed on silica (700 g in a 100 mm column, packed and eluted with 8% (v/v) methanol in methylene chloride), taking 200 mL fractions. The exo isomer of the title amine was obtained in fractions ca. 5–7, and the desired endo isomer in fractions ca. 8–16. TLC was on silica, eluted with 8% methanol-methylene chloride, phosphomolybdic acid stain. The combined product fractions were evaporated to dryness to provide the title compound (4.5 g from each 7 g lot, ca. 18 g total) as a colorless solid.

EXAMPLE B 1-((7,7-Dimethyl-2-oxo-bicyclo(2.2.1)heptan-1-yl) methanesulfonyl)-4-(2-methylphenyl)piperazine

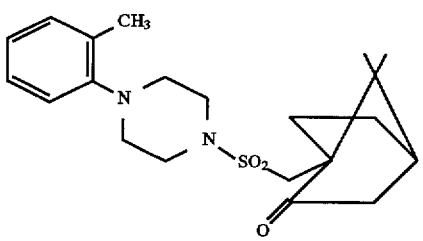

To a stirred, 0° C. solution of 1-(o-tolyl)piperazine hydrochloride (50.0 g; 235 mmol) and TEA (83 mL; 590 mmol) in chloroform (1000 mL) was added (+)-10-camphorsulfonyl chloride (65.5 g; 260 mmol). The solution was stirred at 0° C. for 1 h and then at ambient temperature for 3 h. The solution was extracted with 5% aqueous HCl (2×500 mL), water (500 mL), and saturated aqueous NaHCO$_3$ (2×500 mL). The organic phase was dried (MgSO$_4$), filtered, and the solvent was removed under reduced pressure. The resulting solid was recrystallized from methanol to give the title compound, mp 112°–114° C. (69 g; 75%).

Analysis calculated for ($C_{21}H_{30}N_2O_3S$) C, 64.57; H, 7.74; N, 7.17 Found: C, 64.52; H, 7.68; N, 6.99

TLC: R$_f$0.49 (75:25 hexane/ethyl acetate)

HPLC (method A): retention time 10.33 min

FAB MS: m/z 391 (M$^+$+H)

$^1$H NMR (300 MHz, CDCl$_3$): δ7.2 (m, 2H), 7.0 (m, 2H), 3.45 (m, 4H), 3.40 (d, J=16 Hz, 1H), 3.0 (m, 4H), 2.57 (m, 1H), 2.40 (dt, Jd=14 Hz, Jt=3 Hz, 1H), 2.30 (s, 3H), 2.10 (m, 2H), 1.96 (d, J=14 Hz, 1H), 1.67 (m, 1H), 1.44 (m, 1H), 1.18 (s, 3H), 0.91 (s, 3H)

EXAMPLE 1

(1S)-1'-(((7,7-dimethyl-2-endo-(4-nitrophenyloxycarbonylamino)-bicyclo-(2.2.1)-hept-1-yl)-methyl)-sulfonyl)spiro(1H-indane-1,4'-piperidine)

The product of Example A [3.47 mmol] and 4-nitrophenyl chloroformate [3.64 mmol] were combined in THF. The reaction mixture was treated with triethylamine [4.54 mmol] and allowed to stir for 2 hours. The reaction mixture was concentrated to dryness and the resulting residue was purified by a silica gel column, while eluting with 1% ethyl acetate in methylene chloride. The product fractions were combined and concentrated to dryness in vacuo. The title compound was obtained as a white solid from ether.

EXAMPLE 2

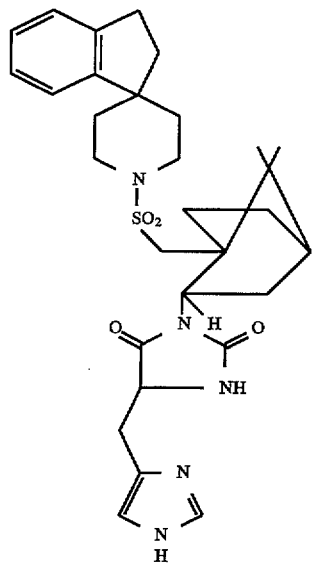

(1S)-1'-(((7,7-dimethyl-2-endo-(4-nitrophenyloxycarbonylamino)-bicyclo-(2.2.1)-hept-1-yl)-methyl))sulfonyl)spiro(1H-indane-1,4'-piperidine) [1.80 mmol] and histidine methyl ester dihydrochloride [1.90 mmol] were combined in DMF. The reaction mixture was treated with triethylamine [5.90 mmol] and allowed to stir for 2 hours. The reaction mixture was concentrated to dryness and the resulting residue was dissolved in CH$_2$Cl$_2$. This CH$_2$Cl$_2$ solution was placed on a silica gel column and eluted with 2% methanol in CH$_2$Cl$_2$ and then with 95/5/0.5 of CH$_2$Cl$_2$/methanol/ammonium hydroxide. The product fractions were combined and evaporated to dryness in vacuo. A white solid was obtained from ether. The resulting white solid [0.954 mmol] and sodium hydride [0.45 mmol] were combined in ethanol and left to stir for 12 hours. The reaction mixture was concentrated to dryness and the resulting residue was dissolved in CH$_2$Cl$_2$. This solution was placed on a silica gel column and eluted with 95/5/0.5 of CH$_2$Cl$_2$/methanol/ammonium hydroxide. The product fractions were combined and evaporated to dryness in vacuo. The title compound was obtained as a white solid from ether and dried in vacuo, overnight.

m.p.: 146° C.–192° C.

NMR: Consistent with structure

HPLC: >99% pure

MS: M+H$^+$=566.2 (FAB)

CHN: Calc'd for $C_{30}H_{39}N_5O_4S$.0.05 $C_4H_{10}O$.0.80 H$_2$O; C, 62.12; H, 7.10; N, 12.00. Found: C, 62.10; H, 7.02; N, 12.01.

EXAMPLE 3

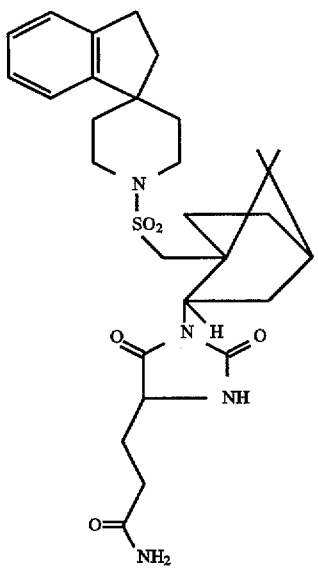

The procedure of Example 2 was carried out using the product of Example 1 [0.197 mmol], triethylamine [0.54 mmol] and substituting glutamine-t-butyl ester hydrochloride [0.217 mmol] for histidinne methyl ester dihydrochloride. Chromatographic elution for column 1 was with 1% methanol in $CH_2Cl_2$ and then with 3% methanol in $CH_2Cl_2$. The title compound was obtained as a white solid from ether and dried in vacuo, overnight.

mp: 104°–166° C.
NMR: Consistent with structure
HPLE: >97% pure
MS: $M+H^+$=557.2 (FAB)
CHN: Calc'd for $C_{29}H_{40}N_4O_5S \cdot 0.50\ C_4H_{10}O \cdot 0.10\ H_{2O}$; C, 62.51; H, 7.65; N, 9.41. Found: C, 62.55; H, 7.36; N, 9.04.

EXAMPLE 4

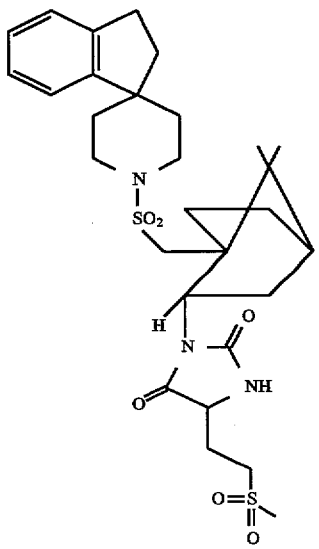

The procedure of Example 2 was carded out using the product of Example 1 [0.215 mmol], triethylamine [0.55 mmol] and substituting L-methionine methyl ester [0.239 mmol] for histidine methyl ester dihydrochloride. Chromatographic elution for column 1 was with 96/4/0.4 of $CH_2Cl_2$/methanol/ammonium hydroxide. For column 2, the elution was done with 5% methanol in $CH_2Cl_2$ and then with 95/5/0.5 of $CH_2Cl_2$/methanol/ammonium hydroxide. A white solid was obtained from ether. This white solid was dissolved in methanol. This solution was treated with oxone [0.284 mmol], which had been dissolved in a small amount of water, and the mixture was stirred at ambient temperature for 4 hours. The reaction mixture was concentrated and the resulting residue was partitioned between ethyl acetate and sat'd sodium bicarbonate solution. The ethyl acetate layer was dried over sodium sulfate, filtered, and the filtrate was concentrated in vacuo. The residue was purified by a silica gel column, eluted with 2% methanol in $CH_2Cl_2$. The product fractions were combined and concentrated. The title compound was obtained as a white solid from ether, and dried in vacuo, overnight.

m.p.: 134°–209° C.
NMR: Consistent with structure
HPLC: >97% pure
MS: $M+H^+$=592 (FAB)
CHN: Calc'd for $C_{29}H_{41}N_3O_6S_2$; C, 58.86; H, 6.98; N, 7.10. Found: C, 58.55; H, 6.59; N, 7.04.

EXAMPLE 5

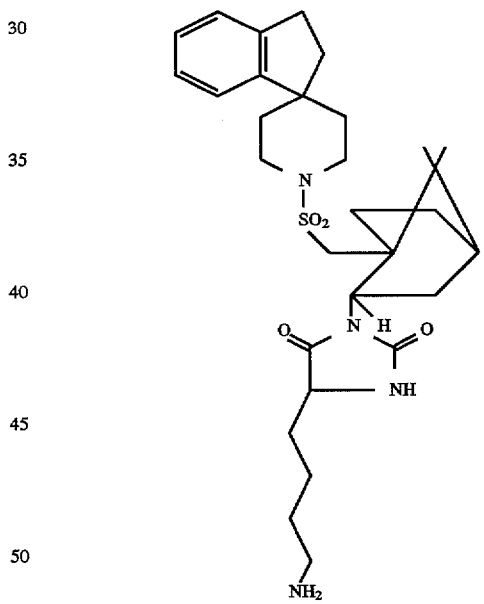

The procedure of Example 2 was carried out using the product of Example 1 [0.366 mmol], triethylamine [0.83 mmol], and substituting N-α-Cbz-L-Lysine methyl ester [0.379 mmol] for histidine methyl ester dihydrochloride. Chromatographic elution for column 1 was with 95/5/0.5 of $CH_2Cl_2$/methanol/ammonium hydroxide. For column 2, the elution was done with 2% methanol in $CH_2Cl_2$. A white solid was obtained from ether. This white solid was combined with palladium hydroxide on carbon catalyst in absolute ethanol. The mixture was hydrogenated at 40 p.s.i. overnight. The reaction mixture was filtered and the filtrate was concentrated to dryness. The resulting residue was purified by a silica gel column, eluting with 92/8/0.8 of $CH_2Cl_2$/methanol/ammonium hydroxide. The product fractions were combined and evaporated to dryness. The title compound was obtained as a white solid from ether and was dried in vacuo, overnight.

m.p.: 99°–158° C.

NMR: Consistent with structure

HPLE: >94% pure

MS: M+H$^+$=557.3 (FAB)

CHN: Calc'd for $C_{30}H_{44}N_4O_4S \cdot 0.25\ C_4H_{10}O \cdot H_2O$; C, 64.11; H, 8.18; N, 9.65. Found: C, 64.12; H, 8.01; N, 9.32.

EXAMPLE 6

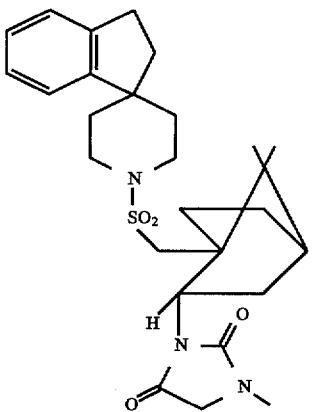

The procedure of Example 2 was carded out using the product of Example 1 [0.33 mmol], triethylamine [0.88 mmol], and substituting L-leucine methyl ester [0.35 mmol] for histidine methyl ester dihydrochloride. Chromatographic elution for column 1 was with 95/5/0.5 of $CH_2Cl_2$/methanol/ammonium hydroxide. For column 2, the elution was done with 1% methanol in $CH_2Cl_2$. The title compound was obtained as a white solid from ether and dried in vacuo, overnight.

106°–128° C.

NMR: Consistent with structure

HPLE: >94% pure

MS: M+H$^+$=542.3 (FAB)

CHN: Calc'd for $C_{30}H_{43}N_3O_4S$; C, 66.51; H, 8.00; N, 7.76. Found: C, 66.24; H, 8.10; N, 7.49.

EXAMPLE 7

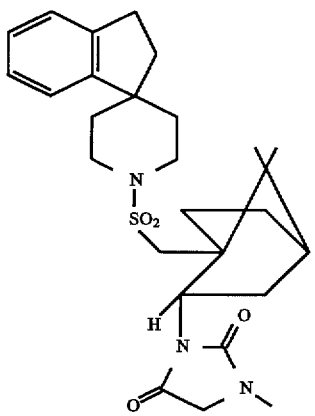

The procedure of Example 2 was carried out using the product of Example 1 [0.23 mmol], triethylamine [0.73 mmol], and substituting sarcosine ethyl ester [0.29 mmol] for histidine methyl ester dihydrochloride. Chromatographic elution for column 1 was with 1% ether in $CH_2Cl_2$ and then with 5% methanol in $CH_2Cl_2$. For column 2, elution was done with 25% ethyl acetate in hexane. The title compound was obtained as a white solid from ether and dried in vacuo, overnight.

m.p.: 89°–152° C.

NMR: Consistent with structure

HPLE: >96% pure

MS: M+H$^+$=500 (FAB)

CHN: Calc'd for $C_{27}H_{37}N_3O_4S \cdot 0.10\ C_4H_{10}O \cdot 0.40\ H_2O$; C, 63.99; H, 7.60; N, 8.17. Found: C, 63.95; H, 7.37; N, 7.92.

EXAMPLE 8

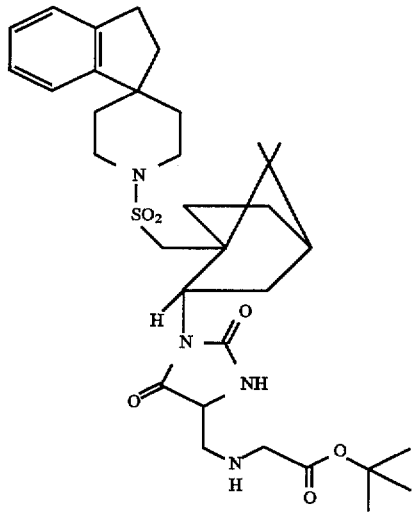

The procedure of Example 2 was carried out using the product of Example 1 [1.16 mmol], triethylamine [1.56 mmol], and substituting methyl(2-amino-3-(t-Boc-amino)) propanoate [1.27 mmol] for histidine methyl ester dihydrochloride. Chromatographic elution for column 1 was with 5% ether in $CH_2Cl_2$ and then with 3% methanol in $CH_2Cl_2$. For column 2, elution was done with 1% methanol in $CH_2Cl_2$. The title compound was obtained as a white solid from ether and dried in vacuo, overnight.

m.p.: 104°–176° C.

NMR: Consistent with structure

HPLE: >97% pure

MS: M+H$^+$=615 (FAB)

CHN: Calc'd for $C_{32}H_{46}N_4O_6S \cdot 0.10\ C_4H_{10}O \cdot 0.45\ H_2O$; C, 61.73; H, 7.66; N, 8.89. Found: C, 61.68; H, 7.66; N, 8.97.

EXAMPLE 9

17

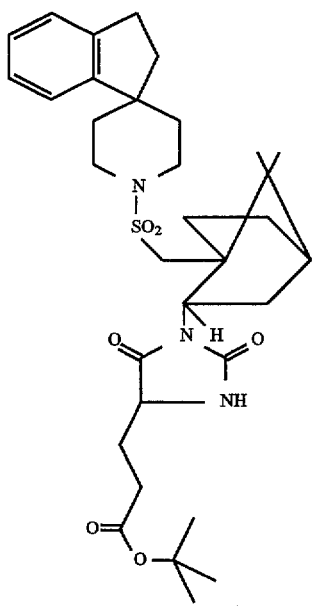

The procedure for Example 2 was carried out using the product of Example 1 [0.27 mmol], triethylamine [0.76 mmol], and substituting glutamic acid-α-methyl ester-α-methyl ester-α-t-butylester [0.308 mmol] for histidine methyl ester dihydrochloride. Chromatographic elution for column 1 was with 5% ether in $CH_2Cl_2$ and then with 5% methanol in $CH_2Cl_2$. For column 2, elution was done with 4% methanol in $CH_2Cl_2$. The title compound was obtained as a white solid from ether and dried in vacuo, overnight.

m.p.: 94°–117° C.

NMR: Consistent with structure

HPLE: >93% pure

MS: $M+H^+$=614 (FAB)

CHN: Calc'd for $C_{33}H_{47}N_3O_6S \cdot 0.10\ C_4H_{10}O \cdot 0.50\ H_2O$; C, 63.65; H, 7.84; N, 6.67. Found: C, 63.68; H, 7.64; N, 6.67.

EXAMPLE 10

18

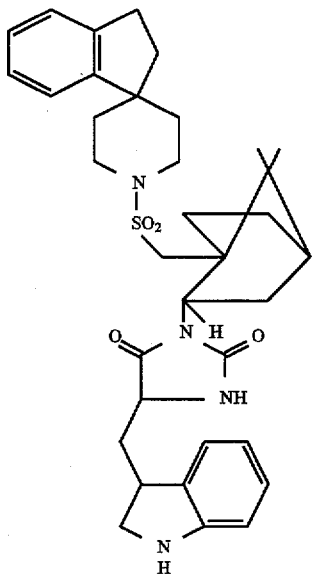

The procedure of Example 2 was carried out using the product of Example 1 [0.22 mmol], triethylamine [0.60 mmol], and substituting D-tryptophan methyl ester [0.24 mmol] for histidine methyl ester dihydrochloride. Chromatographic elution for column 1 was with 1% ether in $CH_2Cl_2$ and then with 5% methanol in $CH_2Cl_2$. For column 2, elution was done with 4% methanol in $CH_2Cl_2$. The title compound was obtained as a white solid from ether and dried in vacuo, overnight.

m.p.: 111°–176° C.

NMR: Consistent with structure

HPLE: >92% pure

MS: $M+H^+$=615.2 (FAB)

CHN: Calc'd for $C_{35}H_{42}N_4O_4S \cdot 0.50\ C_4H_{10}O \cdot 0.85\ H_2O$; C, 66.62; H, 7.29; N, 8.49. Found: C, 66.64; H, 6.93; N, 8.12.

EXAMPLE 11

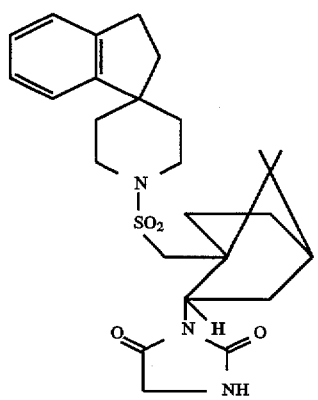

19

The procedure of Example 12 was carried out using the product of Example 1 [1.38 mmol], triethylamine [3.40 mmol], and substituting glycine methyl ester hydrochloride [1.54 mmol] for histidine methyl ester dihydrochloride. Chromatographic elution for column 1 was with 1% ether in $CH_2Cl_2$ and then with 4% methanol in $CH_2Cl_2$. For column 2, the elution was done with 99/1/0.1 of $CH_2Cl_2$/methanol/ammonium hydroxide. The title compound was obtained as a white solid from ether and dried in vacuo, overnight.

m.p.: 230°–239° C.

NMR: Consistent with structure

HPLE: >92% pure

MS: M+H⁺=486 (FAB)

CHN: Calc'd for $C_{26}H_{35}N_3O_4S \cdot 0.10\ C_4H_{10}O \cdot 0.20\ H_2O$; C, 63.84; H, 7.39; N, 8.46. Found: C, 63.77; H, 7.39; N, 8.50.

EXAMPLE 12

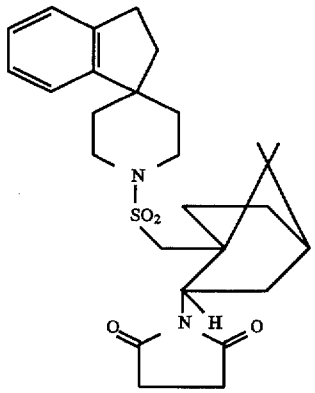

Succinic anhydride (12 mg, 0.12 mmols) and endo-(1S)-1'-(((2-amino-7,7-dimethylbicyclo-(2.2.1)-hept-1-yl) methyl)sulfonyl)spiro(1H-indane-1,4'-piperidine) (50 mg, 0.12 mmols) were combined in a mixture of THF (1 mL) and methylene chloride (1 mL) and stirred at ambient temperature for eighteen hours. The solvents were removed under vacuum and the residue was treated with trifluoroacetic anhydride (1 mL) and toluene (2 mL), then heated to reflux for 15 minutes while the excess trifluoroacetic anhydride was allowed to boil out. The mixture was then cooled and evaporated to dryness in vacuo. The residue was chromatographed on silica gel (8" column, 0.5" diam.), eluted with 0.5% (100 mL) followed by 1% (100 mL) methanol in methylene chloride. The product fractions were combined and evaporated to dryness in vacuo. The residue was dissolved in ethyl acetate, diluted with hexane, and allowed to stand whereupon the title compound was deposited as a white solid. This material was filtered and dried in vacuo at 90° for eighteen hours.

m.p.: 228.5°–229.5° C.

¹H-NMR: Consistent with structure, ca. 0.1 mol of ethyl acetate and ca 0.05 mol of hexane observed TLC: (2% MeOH in $CH_2Cl_2$) single component, $R_f$=0.66

MS: M+H⁺=485 (FAB)

CHN: Calc'd for $C_{27}H_{36}N_2O_4S \cdot 0.10\ C_4H_8O_2 \cdot 0.05\ C_6H_{14}$; C, 66.83; H, 7.59; N, 5.63. Found: C, 66.62; H, 7.61; N, 5.51.

EXAMPLE 13

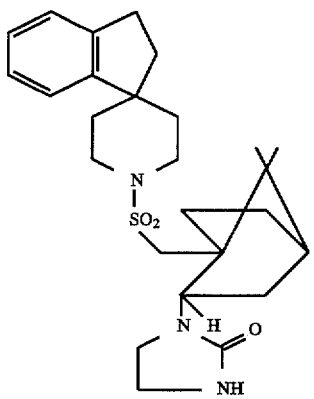

To a 0° C. solution of endo-(1S)-1'(((2-amino-7,7-dimethylbicyclo(2.2.1)-hept-1-yl)-methyl)-sulfonyl)spiro(1H-indan-1,4'-piperidine) (0.90 g; 2.2 mmol) and diisopropylethylamine (DIEA) (0.47 mL; 2.7 mmol) in $CHCl_3$ (50 mL) was added iodoacetonitrile (0.38 grams; 2.3 mmol). The solution was stirred for 1 h at 0° C. and then for 18 h at ambient temperature. The mixture was extracted with aqueous $NaHCO_3$ (2×25 mL), dried ($MgSO_4$), filtered, and the solvent was removed under reduced pressure. The residue was purified by pressurized silica gel column chromatography using 1:3 ethyl acetate-hexanes as eluant (TLC Rf=0.30 in 1:3 ethyl acetate-hexanes; HPLC retention time= 9.30 min). The purified cyanomethylated amine (0.80 g; 1.8 mmol) was dissolved in 2-methoxyethanol (15 mL) and to the stirred solution was added Raney nickel alloy (2.5 grams) followed by 6N NaOH solution (2.0 mL, 12 mmol). The mixture was heated to 8020 C. on a steam bath and then stirred at ambient temperature for 14 h. The catalyst was removed by filtration through Celite and washed with EtOAc. The filtrate solvents were removed under reduced pressure and the residue was taken up in $CHCl_3$ (50 mL) and washed with water (2×25 mL). The organic phase was dried ($MgSO_4$), filtered and concentrated under reduced pressure. The residue was purified by pressurized silica gel column chromatography using 92:8:0.8 $CHCl_3$:MeOH:$NH_4$: OH as eluant (TLC Rf=0.25 in 92:8:0.8 : $CHCl_3$:MeOH:$NH_4OH$; HPLC retention time=7.20 min; FAB mass spectrum m/z= 446). The purified diamine (0.51 g; 1.1 mmol) was dissolved in $CHCl_3$ and to the solution was added 1,1'-carbonyldiimidazole (0.19 g; 1.2 mmol). After the solution had been stirred for 1 h at ambient temperature, acetic acid (0.63 mL; 11 mmol) was added and the solution was refluxed for 6 h. The reaction was cooled and the solvent was removed under reduced pressure. The residue was dissolved in EtOAc (50 mL) and the solution was washed with 10% aqueous citric acid (25 mL), water (25 mL), and aqueous $NaHCO_3$ (25 mL). The organic phase was dried ($MgSO_4$), filtered, and the solvent was removed under reduced pressure. The residue was purified by pressurized silica gel column chromatography using 1:3 EtOAc:$CHCl_3$ as eluant. The title compound was obtained as a white foam from $CHCl_3$ (TLC $R_f$=0.27 in 1:4 EtOAc:$CHCl_3$;

HPLC retention time=10.67 min;

FAB mass spectrum m/z=472; calc for $C_{26}H_{37}N_3O_3S \cdot 0.70\ CHCl_3$: C, 57.76; H, 6.84; N, 7.75. Found: C, 57.84; H, 6.82; N, 7.42;

¹H NMR ($CDCl_3$, 300 MHz) δ7.15–7.25 (m, 4H), 4.39 (ddd, J=2.3, 5.3, 12.0 Hz, 1H) 1.05 (s, 3H), 1.00 (s, 3H)).

HPLC conditions: 12 cm C$_{18}$ reverse phase Vydac column; 15 min gradient 95:5 to 0:100 A:B (A=H$_2$O containing 0.1% TFA, B=CH$_3$CN containing 0.1% TFA), flow rate=2.0 mL/min, detection at 215 nm.

EXAMPLE 14

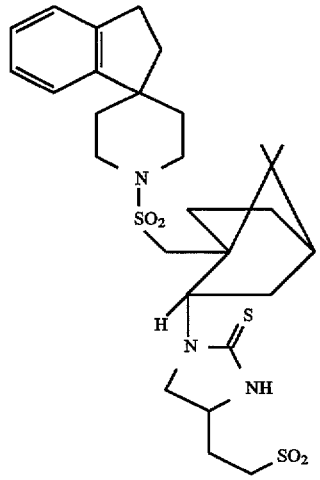

2-Amino-[1-[[(2,3 -dihydrospiro[1H-indene-1,4'-piperidin]-1'-yl)sulfonyl]methyl]-7,7-dimethylbicyclo[2.2.1]hept-2-yl]-4-(methyl-sulfonyl)-but-1-ylamine (250 mg, 0.425 mmole) and thiocarbonyldiimidazole (76 mg, 0.425 mmole) were combined with 500 mg of anhydrous cesium carbonate in 12 ml of dry N,N'-dimethylformamide at room temperature. The orange suspension was stirred for 2 hours, filtered, and concentrated under reduced pressure. The residue was partitioned between ethyl acetate (100 ml) and sodium bicarbonate solution. The phases were separated and the organic phase was washed with saturated sodium bicarbonate solution (3×40 ml) and brine, then dried (sodium sulfate) and concentrated. The crude product was (250 mg) was obtained as an oil which crystallized on standing in methanol NMR: Consistent with structure and verifies presence of solvent;

HPLC: >97% pure at 214 nm;

FAB MS: 594 (M++H);

Elem. Anal. calc'd for C$_{29}$H$_{43}$N$_3$O$_4$S$_3$.1.05 CH$_3$OH.0.25H$_2$O: Calc'd: C, 57.10; H, 7.61; N, 6.65. Found: C, 57.11; H, 7.21; N, 6.28.

EXAMPLE 15

1-[1-[[(2,3-Dihydrospiro[1H-indene-1,4'-piperidin]-1'-yl) sulfonyl]-methyl]-7,7-dimethylbicyclo[2.2.1]hept-2-yl]-2,5-dioxo-3-pyrrolidineacetic acid

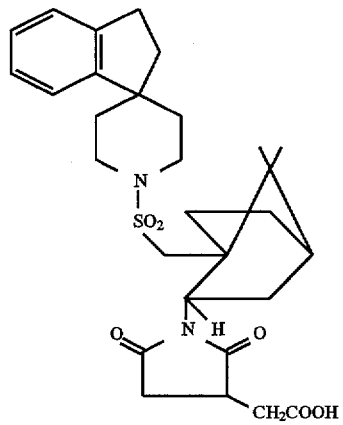

2-Carboxymethylsuccinic anhydride (3-carboxymethyl-tetrahydrofuran-2,5-dione) was prepared from tricarballylic acid as described in J. Org. Chem. 46 2866 (1981). 2-Carboxymethylsuccinic anhydride (0.93 g, 5.88 mmols) and endo-(1S)-1'-(((2-amino-7,7-dimethylbicyclo-(2.2.1)-hept-1-yl)methyl)sulfonyl)-spiro(1H-indene-1,4'-piperidine) (2.4 g, 5.97 mmols) were combined in DMF (20 mL) and stirred at ambient temperature for eighteen hours. The DMF was removed under vacuum and the residue was treated with 1N HCl and extracted with methylene chloride. The methylene chloride layers were combined, dried over sodium sulfate, filtered, and evaporated to dryness in vacuo. The residue was treated with toluene (100 mL) and trifluoroacetic anhydride (5mL), and the resulting mixture was heated to reflux for 2–4 min while the excess trifluoroacetic anhydride was allowed to boil out. Reflux was continued for 10 min, and the mixture was then cooled and evaporated to dryness in vacuo. The residue was chromatographed on silica gel (10" column, 2" diam.), eluted with 200:10:1:1 CH$_2$Cl$_2$:MeOH:HoAc:H$_2$O. The product obtained by evaporation of the eluate was rechromatographed on silica gel twice, once eluted with 1L each of 1000:10:1:1, 500:10:1:1, and 330:10:1:1 CH$_2$Cl$_2$:MeOH:HoAc:H$_2$O, and the second time with 600:10:1:1 of the same solvents. The combined product fractions were evaporated to dryness in vacuo, treated with ether and re-evaporated 3 times, then treated with hexane and evaporated to obtain the title compound as a solid which was dried in vacuo at 400° C. for eighteen hours.

M.P.: 80°–100° C. (foam;indistinct)

HPLC: 100%

$^1$H-NMR: Consistent with structure, ca. 0.05 mol of DMF and ca. 0.18 mol of hexane observed.

TLC: (490:10:1:1 CH$_2$Cl$_2$:MeOH:HoAc:H$_2$O) single component, R$_f$=0.25.

M.S.: (FAB) M+H @543

Analysis for C$_{29}$H$_{38}$N$_2$O.0.05 C$_3$H$_7$NO.0.18 C$_6$H$_{14}$.0.3 H$_2$O: Calc'd: C, 64.00; H, 7.37; N, 5.0 Found: C, 64.01; H, 7.30; N, 5.12.

EXAMPLE 16

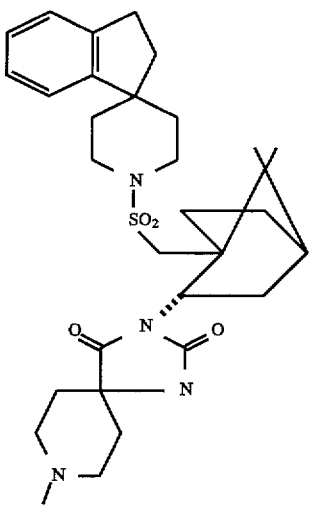

To a 0° C. stirred solution of p-nitrophenyl chloroformate (1.37 g; 6.8 mmol) in CHCl$_3$ (100 mL) was added DIEA (1.18 ml; 12.4 mmol) and the product of Example A (2.5 g; 6.2 mmol). The solution was stirred at 0° C. for 1 h and then at ambient temperature for 14 h. The reaction mixture was concentrated under reduced pressure, the residue was dissolved in CHCl$_3$ (100 mL) and washed with 5% aqueous HCl (2×50 mL) and aqueous NaHCO$_3$ (100 mL). The organic phase was dried (MgSO$_4$), filtered, and the solvent was removed under reduced pressure. The urethane was obtained as a white foam.

TLC: R$_f$ 0.35 (1:3 EtOAc:hexanes)

HPLC (method A): retention time 12.3 min

To a 0° C. stirred solution of the p-nitrophenyl urethane (2.8 g; 5.0 mmol) in DMF (20 mL) was added methyl 1-methyl-4-amino-4-piperidine carboxylate hydrochloride (1.04 gm, 5 mmol) and DIEA (0.87 ml, 5 mmol). The solution was stirred for 2 hours at ambient temperature. The reaction mixture was concentrated under reduced pressure, the residue was dissolved in CHCl$_3$ (100 mL) and washed with 5% aqueous HCl (2×50 mL) and 10 % aqueous Na$_2$CO$_3$ (5×100 mL). The organic phase was dried (MgSO$_4$), filtered, and the solvent was removed under reduced pressure. The urea was obtained as a foam which was crystallized from EtOAc (1.14 gm, 2 mmol).

Analysis calculated for (C$_{31}$H$_{44}$N$_4$O$_4$S).1.85 H$_2$O C 60.61 H 8.22 N 8.84 Found: C 60.58 H 8.02 N 8.80

TLC: R$_f$ 0.2 (95:5:0.5 CHCl$_3$:MeOH:NH$_3$OH)

HPLC (method A): retention time 9.17 min

FAB MS: m/z 601 (M$^+$+H)

To a 0° C. stirred solution of the urea (1.0 gm, 1.67 mmol) in MeOH (50 mL) was added in small portions NaH (dry powder) (0.125 gm, 5 mmol). The solution was stirred for 2 hours. The reaction mixture was neutralized with acetic acid and evaporated under reduced pressure. The residue was dissolved in CHCl$_3$ (100 mL) and washed with 5% aqueous HCl (2×50 mL) and aqueous NaHCO$_3$ (100 mL). The organic phase was dried (MgSO$_4$), filtered, and the solvent was removed under reduced pressure. The title compound was obtained as a foam which was precipitated from EtOAc/hexanes (0.260 gm, 0.5 mmol).

Analysis calculated for (C$_{31}$H$_{44}$N$_4$O$_4$S).0.3 EtOAc C 64.98 H 7.86 N 9.41 Found: C 64.65 H 7.76 N 9.46

TLC: R$_f$ 0.35 (95:5:0.5 CHCl$_3$MeOH:NH$_4$OH)

HPLC (method A): retention time 10.17 min

FAB MS: m/z 569 (M$^+$+H)

$^1$H NMR (300 MHz, CDCl$_3$): d 7.15–7.25 (m, 4H), 5.8 (s, 1H), 4.49 (m, 1H), 2.3 (s, 3H), 1.02 (s, 3H), 0.97 (s, 3H)

EXAMPLE 17

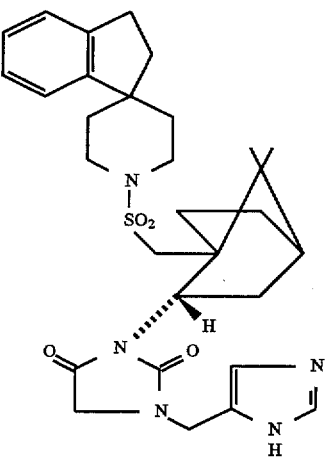

To a 0° C. solution of the unsubstituted hydantoin product of Example 11 (1.50 g; 3.09 mmol) and 4-chloromethyl-1-(triphenyl)methylimidazole (1.39 g; 3.87 mmol) in dry THF (60 mL) under an atmosphere of argon was added NaH (154 mg of a 60% suspension in mineral oil; 3.86 mmol). The mixture was stirred at 0° C. for 1 h, and then at ambient temperature for 24 h. Several drops of acetic acid were added and the mixture was concentrated under reduced pressure. The residue was dissolved in EtOAc (100 mL) and washed with aqueous NaHCO$_3$ (2×50 mL). The organic phase was dried (MgSO$_4$), filtered and concentrated under reduced pressure. The residue was purified by pressurized silica gel column chromatography using 1:1 EtOAc:CHCl$_3$ as eluant. The product (1.40 g; 1.73 mmol) was heated in 10 mL of MeOH containing 10 mL of 6N HCl at 60° C. for 6 h. The solvents were removed under reduced pressure and the residue was dissolved in CHCl$_3$ (100 mL) and washed with aqueous NaHCO$_3$ (2×50 mL). The organic phase was dried (MgSO$_4$), filtered, and concentrated under reduced pressure. The residue was purified by pressurized silica gel column chromatography using 95:5:0.5 CHCl$_3$:MeOH:NH$_4$OH as eluant. The purified product was dissolved in MeOH containing 3 equivalents of 6N HCl and the solvent was removed under reduced pressure. The residue was taken up in water-dioxane and lyophilized to give the HCl salt of title compound as a white powder.

Analysis calculated for (C$_{30}$H$_{39}$N$_5$O$_4$S).2.05 HCl.0.55 H$_2$O C, 57.40; H, 6.53; N, 10.77 Found: C, 57.44; H, 6.53; N, 10.41

TLC: R$_f$ 0.29 (95:5:0.5 CHCl$_3$:MeOH:NH$_4$OH)

HPLC (method A): retention time 9.43 min

FAB MS: m/z 566 (M$^+$+H)

$^1$H NMR (300 MHz, CDCl$_3$): δ8.95 (s, 1H), 7.40 (s, 1H), 7.15–7.25 (m, 4H), 4.75 (m, 2H), 4.55 (m, 1H), 1.03 (s, 3H), 0.97 (s, 3H)

EXAMPLE 18

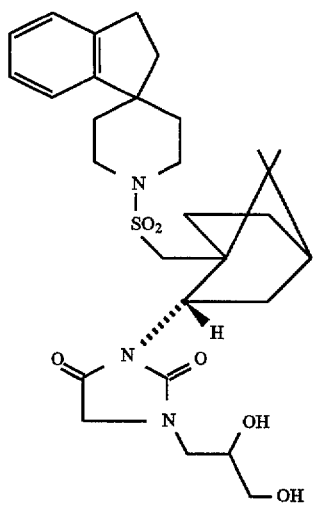

To a stirred solution of the hydantoin (150 mg; 0.309 mmol) in a mixture of 2:1 allyl bromide:tetrahydrofuran (30 mL) was added sodium hydride (12 mg; 60% dispersion in oil). The temperature was then increased to reflux. After 1 hr the solution was cooled, then concentrated. Purification by flash chromatography (5% methanol in methylene chloride) provided the intermediate allyl derivative (158 mg).

The allyl hydantoin described above (105 mg; 0.20 mmol) was dissolved in a solution of 1:1 pyridine:toluene (12 mL). While stirring at room temperature, osmium tetraoxide (51 mg; 0.20 mmol) was added. After 8 hr 10 mL of a saturated aqueous solution of sodium bisulfite was added. The solution was allowed to stir for 1 hr, then diluted with ethyl acetate (50 mL). The ethyl acetate was separated, dried over sodium sulfate, then concentrated. Purification of the residue by flash chromatography (10% methanol in methylene chloride) afforded the title compound (39 mg; 35%).

Analysis calculated for $(C_{29}H_{41}N_3O_6S).0.56\ H_2)$ C, 61.13; H, 7.45; N, 7.37 Found: C, 61.15; H, 7.55; N, 7.15

HPLC (Vydac C18 Column; gradient from 95/5 to 0/100 $H_2O/CH_3CN$ with 0.1% TFA. 15 min. gradient, flow rate= 1.5 ml/min.) $R_t$=12.12 min. Purity=96%

$^1$HNMR: Consistent with structure

FABMS: m/z=560 $(M^++H)$

EXAMPLE 19

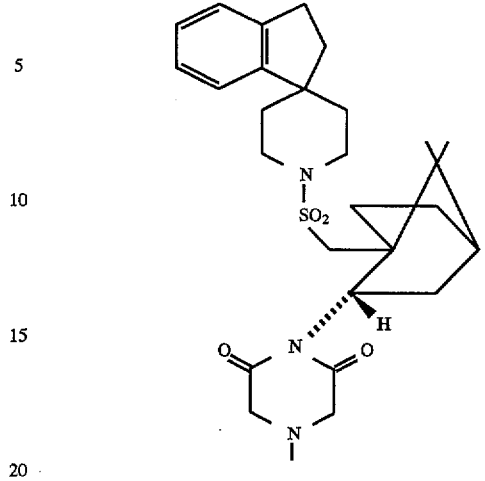

To a stirred solution of N-methyliminodiacetic acid (220 mg; 1.50 mmol) in DMF (10 mL) was added DIEA (0.575 mL; 3.30 mmol) and BOP (665 mg; 1.50 mmol). The mixture was stirred at ambient temperature for 24 h, and then the product of Example A (500 mg; 1.24 mmol) was added. The mixture was stirred at ambient temperature for 24 h and then the solvent was removed under reduced pressure. The residue was dissolved in EtOAc (50 mL) and washed with 10% aqueous citric acid (20 mL) and water (10 mL). The organic phase was dried $(MgSO_4)$, filtered, and the solvent was removed under reduced pressure. The residue was purified by pressurized silica gel column chromatography using a gradient elution of 5–10% MeOH—$CHCl_3$. The purified monoacid, monoamide was obtained as a white foam.

TLC: $R_f$ 0.40 (90:10 $CHCl_3$:MeOH)

HPLC (method A): retention time 9.03 min

FAB MS: m/z 532 $(M^++H)$

The purified monoacid, monoamide (150 mg; 0.282 mmol) was heated to reflux in a solution of THF (5 mL) and acetic anhydride (1mL) for 14 h. The solvents were removed under reduced pressure and the residue was purified by pressurized silica gel column chromatography using 1:4 EtOAc-hexanes as eluant. The title compound was obtained as a white foam from ether.

Analysis calculated for $(C_{28}H_{39}N_3O_4S).0.2$ ether.0.1 $H_2O$ C, 65.23; H, 7.83; N, 7.92; Found: C, 65.10; H, 7.99; N, 7.95;

TLC: $R_f$ 0.29 (1:2 EtOAc:hexanes)

HPLC (method A): retention time 10.57 min

FAB MS: m/z 514 $(M^++H)$ $^1$H NMR (300 MHz, $CDCl_3$): $\delta$ 7.10–7.25 (m, 4H), 5.20 (ddd, J=2.2, 5.9, 12.1 Hz, 1H), 3.40 (s, 3H), 2.37 (s, 3H), 1.06 (s, 3H), 0.95 (s, 3H)

EXAMPLE 20

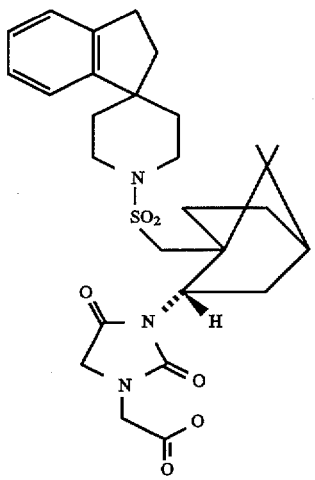

(1S)-1'-(((2-endo-Amino-7,7-dimethylbicyclo-(2.2.1)hept-1-yl)methyl)sulfonyl)spiro(1H-indane-1,4'-piperidine) (1.5 g, 3.7 mmole), tert-butylbromo acetate (0.8 g, 4.1 mmole), and crushed potassium carbonate (0.57 g, 4.1 mmole) were combined in 80 ml of absolute ethanol and heated at reflux for 12 hours. The reaction mixture was cooled, filtered, and rotoevaporated under reduced pressure. The residual material was partitioned between ethyl acetate and water. The phases were separated and the organic layer was washed in succession with saturated sodium bicarbonate solution and brine, then dried (sodium sulfate), and concentrated to give a semi-solid. The crude product was crystallized from ethyl acetate to give 0.85 g of (1S)-1'-(((2-endo-tert-butyloxycarbonylmethylamino-7,7-dimethylbicyclo-(2.2.1) hept-1-yl)methyl)sulfonyl)spiro(1H-indane-1,4'-piperidine). Concentration of the mother liquors afforded an additional 0.99 g of material.

A solution of 40 ml of methylene chloride containing 0.41 ml of triethylamine and 0.97 g of (1S)-1'-(((2-endo-tert-butyloxycarbonylmethylamino-7,7-dimethylbicyclo(2.2.1) hept-1-yl)methyl)sulfonyl)spiro(1H-indane-1,4'-piperidine) was stirred magnetically in an ice bath and treated in one portion with 0.24 ml of bromoacetylbromide. After 1 hour, an additional equivalent each of bromoacetylbromide and triethylamine were added and the reaction mixture was stirred at ambient temperature overnight. The reaction mixture was diluted with methylene chloride and washed in succession with sodium bicarbonate solution, 10% citric acid solution, and brine. The dried extracts were concentrated and the residual material was flash chromatographed on silica gel (15% ethyl acetate-hexane) to give 0.74 g of 2-tert-butyloxycarbonylmethylamino-N-[1-[[(2,3-dihydrospiro[1H-indane-1,4'-piperidin]-1'-yl)sulfonyl]methyl]-7,7-dimethyl-bicyclo[2.2.1]hept-2-yl]-bromoacetamide.

A continuous stream of ammonia gas was passed for 10 minutes into an ice cold solution of methanol (32 ml) containing 0.64 g (1.0 mmole) of 2-tert-butyloxycarbonylmethylamino-N-[1-[[(2,3-dihydrospiro [1H-indane-1,4'-piperidin]-1'-yl)sulfonyl]-methyl]-7,7-dimethylbicyclo[2.2.1]hept-2-yl]-bromoacetamide. The reaction mixture was warmed to room temperature and stirred for 1 hour. All volatile components were removed under reduced pressure to give a semi-solid which was partitioned between ethyl acetate and water. The organic phase was washed with water (3×) and brine, then dried (sodium sulfate) and concentrated. Triturate of the residual material with ether gave 0.32 g of the title compound as an off-white solid m.p. >220° C.;

NMR: Consistent with structure:

HPLC: >99% pure at 214 nm;

FAB MS: 500 (M$^+$+H);

Elem. Analysis calculated for $C_{27}H_{37}N_3O_4S \cdot 0.25\ H_2O$: C, 64.31; H, 7.51; N, 8.34. Found: C, 64.32; H, 7.34; N, 8.14.

EXAMPLE 21

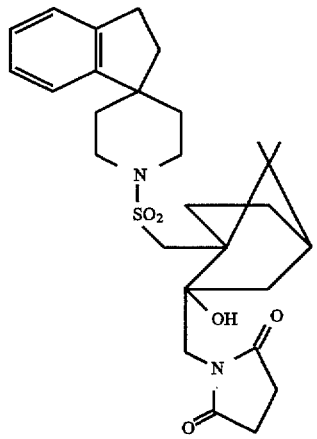

To an ice cold suspension of trimethylsulfoxonium iodide (610 mg, 2.77 mmole) in 10 ml of dry tetrahydrofuran was added 1.8 ml of 1.6M n-butyllithium under nitrogen. After addition was complete the resulting reaction mixture was stirred at ambient temperature for 2 hours, re-cooled to 0° C., and treated with a tetrahydrofuran solution (6 ml) containing 620 mg (1.55 mmole) of (1S)-1'-(((7,7-dimethyl-2-oxobicyclo[2.2.1]hept-1-yl)methyl)sulfonyl)spiro(1H-indene-1,4'-piperidine). The reaction mixture was then stirred at ambient temperature overnight. The reaction mixture was concentrated under reduced pressure to a volume of 6 ml and chromatographed on silica gel (hexane-ethyl acetate, 4:1) separating unreacted starting material and affording 390 mg of (1S)-1'-(((7,7-dimethyl-2-oximinobicyclo-[2.2.1]hept-1-yl)methyl)sulfonyl)spiro-(1H-indene-1,4'-piperidine).

To a suspension of 1.7 mmole of sodium hydride in 1.7 ml of dry N,N'-dimethylformamide was added 0.18 mmole of succinimide. After stirring for 15 minutes the reaction mixture became homogeneous and 70 mg (0.17 mmole) of (1S)-1'-(((7,7-dimethyl-2-oximinobicyclo-[2.2.1]hept-1-yl) methyl)sulfonyl)spiro-(1H-indene-1,4'-piperidine) was added. The reaction mixture was heated at 150° C. for 4 hours, then cooled to room temperature, and diluted with ethyl acetate. The organic phase was washed with water and brine, then dried, and concentrated to give 92 mg of crude product. Flash column chromatography on silica gel (30% ethyl acetate-hexane elution) of the crude reaction product afforded the title compound in analytically pure form as a white solid m.p. 111°–115° C.;

NMR: Consistent with structure:

HPLC: >99% pure at 214 nm;

FAB MS: 513 (M$^+$+H), 621 (M$^+$+thioglycerol);

Elem. Analysis calculated for $C_{28}H_{36}N_2O_5S \cdot 0.75\ H_2O$ C, 63.90; H, 7.20; N, 5.32. Found: C, 63.86; H, 7.14; N, 5.10.

EXAMPLE 22

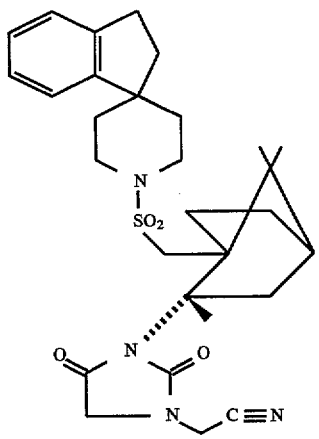

To a 0° C. solution of the unsubstituted hydantoin product of Example 11 (1.50 g; 3.09 mmol) and iodoacetonitrile (1.03 g; 6.18 mmol) in dry THF (30 mL) under an atmosphere of argon was added NaH (185 mg of a 60% suspension in mineral oil; 4.64 mmol). The mixture was stirred at 0° C. for 1 h, and then at ambient temperature for 6 h. The reaction was cooled to 0° C. and more iodoacetonitrile (0.52 g; 3.1 mmol) and NaH (124 mg of a 60% suspension in mineral oil; 3.1 mmol) were added. The mixture was stirred at 0° C. for 1 h, and then at ambient temperature for 14 h. Several drops of acetic acid were added and the dark brown mixture was concentrated under reduced pressure. The residue was dissolved in EtOAc (100 mL) and washed with aqueous NaHCO$_3$ (2×50 mL). The organic phase was dried (MgSO$_4$), filtered and concentrated under reduced pressure. The residue was purified by pressurized silica gel column chromatography using 7:3 hexane:EtOAc as eluant, and then by preparative reverse phase HPLC using a water-acetonitrile gradient containing 0.1% TFA. The title compound was obtained as a lyophilized powder.

Analysis calculated for (C$_{28}$H$_{36}$N$_4$O$_4$S).0.35 TFA.0.25 H$_2$O C, 60.51; H, 6.44; N, 10.22 Found: C, 60.57; H, 6.53; N, 9.85.

TLC: R$_f$0.43 (3:2 hexane:EtOAc)

HPLC (method A): retention time 11.39 min

FAB MS: m/z 525 (M$^+$+H)

$^1$H NMR (300 MHz, CDCl$_3$): δ7.1–7.3 (m, 4H), 4.56 (m, 1H), 4.35 (AB quartet, J=18 Hz, 2H), 3.95 (AB quartet, J=16 Hz, 2H), 1.06 (s, 3H), 0.97 (s, 3H)

EXAMPLE 23

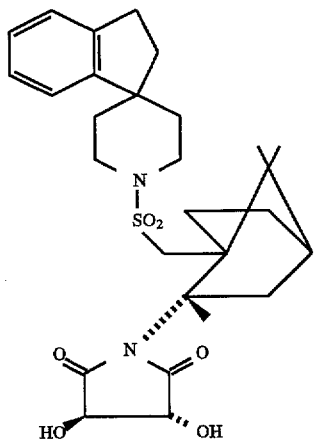

To a stirred solution of endo-(1S)-1'(((2-amino-7,7-dimethylbicyclo(2.2.1)-hept-1-yl)-methyl)-sulfonyl)spiro (1H-indan-1,4'-piperidine (526 mg; 1.31 mmol) in methylene chloride (20 mL) was added diacetyl-L-tartaric anhydride (312 mg; 1.44 mmol), followed by diisopropylethyl amine (0.251 mL; 1.44 mmol). After 18 hr the solution was concentrated, then partitioned between ethyl acetate (200 mL) and 1M HCl (200 mL). The ethyl acetate layer was washed with additional water (2×200 mL), then dried over sodium sulfate and concentrated. Partial purification by flash chromatography (10% methanol in methylene chloride) afforded material that was dissolved in methylene chloride (20 mL) and treated with thionyl chloride (0.096 mL; 1.31 mmol). After stirring at room temperature for 18 hr, the solution was concentrated. The intermediate diacetate was obtained by purification of the residue by flash chromatography (10% methanol in methylene chloride).

The diacetate described above (1 g; 1.66 mmol) was dissolved in a solution of 3:1 tetrahydrofuran:water (40 mL) then cooled to 0° C. A solution of 30% hydrogen peroxide (0.832 mL; 6.64 mmol) was added followed by lithium hydroxide (80 mg; 3.32 mmol). After stirring at 0° C. for 30 min the solution was concentrated. The title compound (492 mg; 73%) was obtained through purification of the residue by flash chromatography (10% methanol in methylene chloride).

Analysis calculated for (C$_{27}$H$_{36}$N$_2$O$_6$S).0.35 H$_2$O C, 62.01; H, 7.07; N, 5.36 Found: C, 62.00; H, 6.86; N, 5.47

HPLC: (Vydac C18 Column; gradient from 95/5 to 0/100 H$_2$O/CH$_3$CN with 0.1% TFA. 15 min. gradient, flow rate=1.5 ml/min.) R$_t$=12.5 min. Purity=100%

$^1$HNMR: Consistent with structure

FABMS: m/z=517 (M$^+$+H)

EXAMPLE 24

[1R-[[(2,3-Dihydrospiro[1H-indene-1,4'-piperidin]-1'-yl)sulfonyl]-methyl]7,7-dimethylbicyclo[2.2.1]hept-2-endo-yl]-3-[2-propen-1-yl]-2,5-dioxo-1-imidazolidine

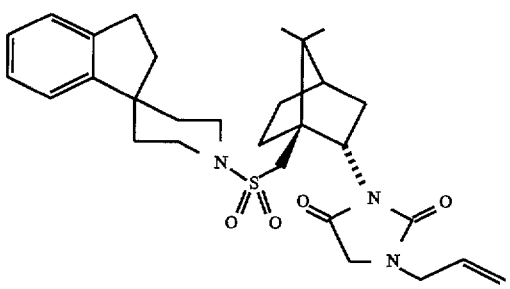

To a stirred solution of [1R-[[(2,3-Dihydrospiro[1H-indene-1,4'-piperidin]-1'-yl)sulfonyl]-methyl]7,7-dimethylbicyclo[2.2.1]hept-2-endo-yl]-2,5-dioxo-1-imidazolidine (150 mg; 0.309 mmol) in tetrahydrofuran (20 mL) was added allyl bromide (27 µL; 0.309 mmol), followed by sodium hydride (12 mg; 60% dispersion in oil). The temperature was increased to reflux. After 4 h the solution was cooled then concentrated. Purification by flash chromatography (5% methanol in methylene chloride) provided the title compound as a white solid (81 mg).

1HNMR: consistent with structure.

M.P.: 101°–104° C.

HPLC: Rt=14.7 min; 95%

FABMS: M+1 at 526

Analysis calculated for $C_{29}H_{39}N_3O_4S+0.05\ CH_2Cl_2+0.40\ H_2O$ C, 64.95; H, 7.49; N, 7.82 Found: C, 64.93; H, 7.48; N, 7.43

EXAMPLE 25

[1R-[[(2,3-Dihydrospiro[1H-indene-1,4'-piperidin]-1'-yl)sulfonyl]-methyl]7,7-dimethylbicyclo[2.2.1]hept-2-endo-yl]-3-[2-hydroxy-3-[1,1-dimethylamino]-propan-1-yl]-2,5-dioxo-1-imidazolidine

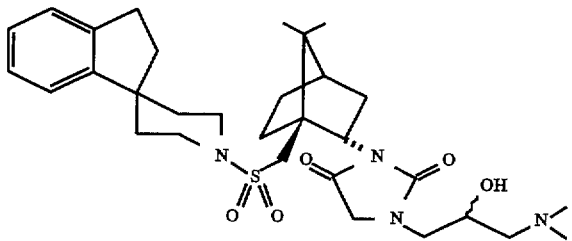

To a stirred solution of [1R-[[(2,3-Dihydrospiro[1H-indene-1,4'-piperidin]-1'-yl)sulfonyl]-methyl]7,7-dimethylbicyclo[2.2.1]hept-2-endo-yl]-2,5-dioxo-1-imidazolidine (164 mg; 0.338 mmol) in tetrahydrofuran (2 mL) was added bromoepihydrin (1 mL), followed by sodium hydride (12 mg; 60% dispersion in oil). The mixture was then heated to reflux. After 6 hours, the mixture was cooled and concentrated. Purification by flash chromatography (30% ethyl acetate in petroleum ether as eluent) afforded [1R-[[(2,3-Dihydrospiro[1H-indene-1,4'-piperidin]-1'-yl)sulfonyl]-methyl]7,7-dimethylbicyclo[2.2.1]hept-2-endo-yl]-3-[2,3 oxirane-1-propenyl]-2,5-dioxo-1-imidazolidine as a white foam (141 mg).

To a solution of [1R-[[(2,3-Dihydrospiro[1H-indene-1,4'-piperidin]-1'-yl)sulfonyl]-methyl]7,7-dimethylbicyclo[2.2.1]hept-2-endo-yl]-3-[2,3 oxirane-1-propenyl]-2,5-dioxo-1-imidazolidine (73 mg; 0.135 mmol) in absolute ethanol (2 mL) was added dimethylamine hydrochloride (55 mg; 0.68 mmol) and diisopropylethylamine ((47 µL). After 6 hours at reflux, the solution was cooled and concentrated. Purification by preparative HPLC afforded the title compound (41 mg).

1HNMR: consistent with structure.

M.P.: 93°–97° C.

HPLC: Rt=11.63 min; 99%

FABMS: M+1 at 587

Analysis calculated for $C_{31}H_{46}N_4O_5S+0.65\ CH_2Cl_2+0.20\ H_2O$ C, 58.88; H, 7.45; N, 8.08 Found: C, 58.90; H, 7.46; N, 8.53

EXAMPLE 26

[1R-[[(2,3-Dihydrospiro[1H-indene-1,4'-piperidin]-1'-yl)sulfonyl]-methyl]7,7-dimethylbicyclo[2.2.1]hept-2-endo-yl]-3-[2,5-dioxo-3S-[4-aminopropylamido]]-1-succinimide

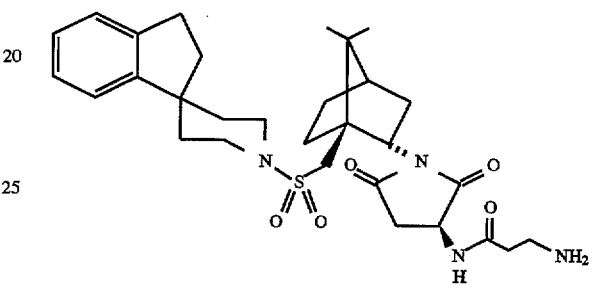

To a solution of endo-[1S]-1'[[[2-amino-7,7-dimethylbicyclo[2.2.1]-hept-1yl]-methyl]-sulfonyl]spiro[1H-indan-1-4'-piperidine](1 g, 2.48 mmol) in methylene chloride (75 mL) was added Boc-(L)-Aspartic acid β-methyl ester (675 mg, 2.72 mmol), hydroxybenzotriazole (436 mg, 3.22 mmol), and 1-(3-dimethylaminopropyl)-3-ethylcarbodiimide hydrochloride (618 mg, 3.22 mmol). After 4 hours the solution was concentrated, then partitioned between ethyl acetate and 1M NaOH (75 mL each). The organic layer was washed with 1M HCl, and brine (75 mL each) then dried over $Na_2SO_4$. The solution was filtered and concentrated. Purification by flash chromatography (40% ethyl acetate in petroleum ether as eluent) gave an amide ester intermediate as white foam (1.15 g).

The foam was dissolved in dry tetrahydrofuran (100 mL) under nitrogen atmosphere, then cooled to –78° C. Lithium hexamethyldisilylazide (3.64 mL, 1M solution in tetrahydrofuran) was added dropwise. After 4 hours, a saturated solution of ammonium chloride was added, and the reaction mixture was allowed to warm to room temperature. The mixture was partitioned between ethyl acetate and water (75 mL each). The ethyl acetate layer was dried over sodium sulfate, then concentrated. Purification by flash chromatography (gradient from 15% to 20% ethyl acetate in petroleum ether as eluent) afforded a protected aminosuccinimide intermediate as a white foam (1.1 g).

To a solution of the aminosuccinimide (1.46 g, 2.43 mmol) in ethyl acetate (50 mL) was introduced a stream of HCl gas. After 15 min. the HCl was removed and the solution was washed with 1M sodium carbonate. The ethyl acetate layer was dried over sodium sulfate, filtered, and concentrated. Purification by flash chromatography (a gradient from 2% to 10% methanol in methylene chloride as eluent) afforded an intermediate unprotected aminosuccinimide as a white foam (1.12 g).

To a solution of the unprotected aminosuccinimide (90 mg, 0.18 mmol) in methylene chloride (15 mL) was added Boc-b-alanine (51 mg, 0.27 mmol), hydroxybenzotriazole (37 mg, 0.27 mmol), 1-(3-dimethylaminopropyl)-3-ethylcarbodiimide hydrochloride (52 mg, 0.27 mmol), and diisopropylethylamine (47 μL, 0.27 mmol). After stirring at room temperature for 6 hours the mixture was concentrated, then partitioned between ethyl acetate and 1M HCl (200 mL each). The ethyl acetate layer was dried over sodium sulfate, then filtered and concentrated. Purification by preparative HPLC afforded an adduct which was dissolved in methylene chloride (20 mL) and treated with trifluoroacetic acid (8 mL). After 1 hour, the solution was concentrated, then the product was purified by preparative HPLC to give the title compound (71 mg).

$^1$HNMR: consistent with structure.

HPLC: R$_t$=12.2 min; 97%

FABMS: M+1 at 571

Analysis calculated for C$_{30}$H$_{42}$N$_4$O$_5$S+2.5 trifluoroacetic acid C, 46.89; H, 5.47; N, 6.83 Found: C, 46.91; H, 5.30; N, 6.77

EXAMPLE 27

[1R-[[(2,3-Dihydrospiro[1H-indene-1,4'-piperidin]-1'-yl)sulfonyl]-methyl]7,7-dimethylbicyclo[2.2.1]hept-2-endo-yl]-3 endo-[2,5-dioxo-3S-amino-[4-piperidinyl]]-1-succinimide

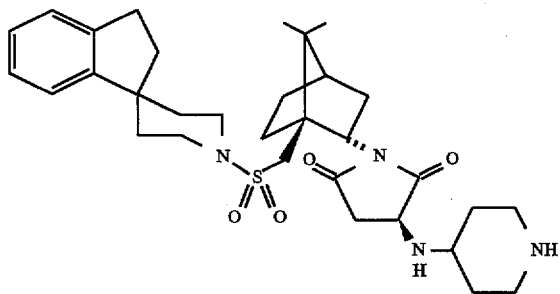

To a solution of [1R-[[(2,3-Dihydrospiro[1H-indene-1,4'-piperidin]-1'-yl)sulfonyl]-methyl]7,7-dimethylbicyclo[2.2.1]hept-2-endo-yl]-3 endo-[2,5-dioxo-[3S-amino]]-1-succinimide (161 mg, 0.32 mmol) in methanol (15 mL) was added Boc-4-piperidinone (77 mg, 0.39 mmol), and sodium cyanoborohydride (61 mg, 0.96 mmol). After stirring at room temperature for 4 hours, the mixture was concentrated and purified by flash chromatography (5% methanol in methylene chloride as eluent).

The residue was redissolved in methylene chloride (10 mL), then treated with trifluoroacetic acid (5 mL). After 2 hours the solution was concentrated. Purification by flash chromatography (10% methanol in methylene chloride as eluent) afforded the title compound (91 mg).

$^1$HNMR: consistent with structure.

HPLC: R$_t$=13.2 min; 98%

FABMS: M+1 at 583

Analysis calculated for C$_{32}$H$_{46}$N$_4$O$_4$S+1.5 trifluoroacetic acid+1.5 H$_2$O C, 53.84; H, 6.52; N, 7.18 Found: C, 53.85; H, 6.69; N, 6.79

EXAMPLE 28

[1R-[[4-(2-methylphenyl)piperazin-1-yl)sulfonyl]-methyl] 7,7-dimethylbicyclo[2.2.1]hept-2-endo-yl]-3-[2R-hydroxy-3-[piperazin-1-yl]-propan-1-yl]-2,5-dioxo-1-imidazolidine

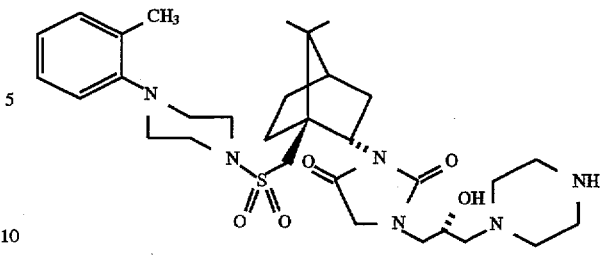

To a stirred solution of [1R-[[4-(2-methylphenyl)piperazin-1-yl)sulfonyl]-methyl]7,7-dimethylbicyclo[2.2.1]hept-2-endo-yl]-2,5-dioxo-1-imidazolidine (120 mg, 0.253 mmol) in dry tetrahydrofuran (15 mL) was added 2R-(–)-glycidyl tosylate (288 mg, 1.26 mmol), followed by sodium hydride (60% dispersion in oil). The temperature was increased to reflux. After 2 hours the mixture was cooled then concentrated. Purification by preparative TLC (40% ethyl acetate in petroleum ether as eluent) afforded [1R-[[4-(2-methylphenyl)piperazin-1-yl)sulfonyl]-methyl]7,7-dimethylbicyclo[2.2.1]hept-2-endo-yl]-3-[2S,3 oxirane-1-propenyl]-2,5-dioxo-1-imidazolidine as a white foam (112 mg).

To a solution of [1R-[[4-(2-methylphenyl)piperazin-1-yl)sulfonyl]-methyl]7,7-dimethylbicyclo[2.2.1]hept-2-endo-yl]-3-[2S,3 oxirane-1-propenyl]-2,5-dioxo-1-imidazolidine (66 mg, 0.12 mmol) in absolute ethanol (20 mL) was added piperazine (50 mg, 0.58 mmol).

The temperature was increased to reflux. After 2 hours the solution was cooled and concentrated. Purification by flash chromatography (85:15:1 methylene chloride:methanol:ammonium hydroxide as eluent) afforded the title compound (19 mg).

$^1$HNMR: consistent with structure.

HPLC: Rt=10.4 min; 95%

FABMS: M+1 at 517

Analysis calculated for C$_{31}$H$_{48}$N$_6$O$_5$S+0.15 hexanes+1.2 H$_2$O C, 58.82; H, 8.12; N, 12.90 Found: C, 58.84; H, 7.76; N, 12.54

EXAMPLE 29

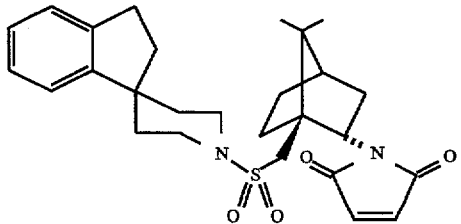

To a solution of endo-(1S)-1'(((2-amino-7,7-dimethyl-bicyclo(2.2.1)-hept-1-yl)-methyl)-sulfonyl)spiro(1H-indan-1,4'-piperidine) (3 g, 7.45 mmol) in methylene chloride (150 mL) was added maleic anhydride (876 mg, 8.94 mmol). After stirring for 2 h at room temperature, the mixture was concentrated, then redissolved in acetic anhydride (100 mL). Sodium acetate was added (611 mg, 7.45 mmol), then the temperature was increased to reflux. After 48 h, the mixture was cooled to room temperature, then concentrated. Flash chromatography using 50% ethyl acetate in petroleum ether afforded 1.5 g of the title compound as a white foam.

$^1$HNMR: consistent with structure.

HPLC: method A, R$_t$=14.86 min; 96%

FABMS: M+1 at 483

Analysis calculated for C$_{27}$H$_{34}$N$_2$O$_4$S+0.35 dioxane C, 66.43; H, 7.22; N, 5.46 Found: C, 66.45; H, 7.25; N, 5.23

EXAMPLE 30

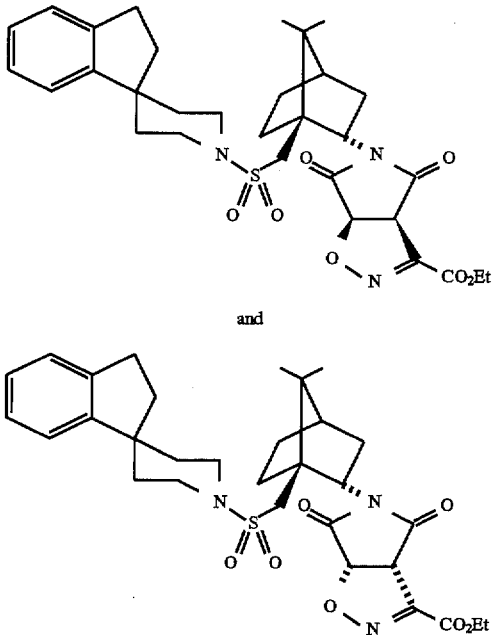

and

To a solution of the product of Example 29 (84 mg, 0.17 mmol) in 1:1 methylene chloride:diethyl ether (15 mL) was added chloroximidoacetate (32 mg, 0.21 mmol), followed by diisopropylethylamine (37 uL). The mixture was allowed to stir at room temperature for 4 h at which time additional chloroximidoacetate was added (32 mg). After 18 h, the mixture was concentrated and the residue was applied to preparative TLC plates. Two products were obtained as white solids, in 40% overall yield.

$^1$HNMR: consistent with structure.

HPLC: method A, R$_t$=14.73 min; 100%

FABMS: M+1 at 598

Analysis calculated for C$_{31}$H$_{39}$N$_3$O$_7$S+0.55 chloroform C, 57.21; H, 5.87; N, 6.34 Found: C, 57.18; H, 5.88; N, 6.41

$^1$HNMR: consistent with structure.

HPLC: method A, R$_t$=14.99 min; 100%

FABMS: M+1 at 598

Analysis calculated for C$_{31}$H$_{39}$N$_3$O$_7$S+0.20 chloroform C, 60.29; H, 6.36; N, 6.76 Found: C, 60.27; H, 6.29; N, 6.72

EXAMPLE 31

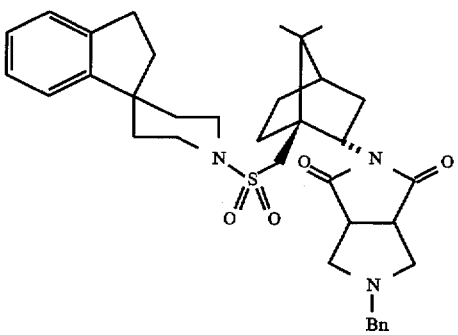

To a solution of the product of example 29 (109 mg, 0.23 mmol) in acetonitrile (10 mL) was added silver iodide (57 mg, 0.46 mmol), followed by a solution of N-benzyl-N-(trimethylsilylmethyl)aminoacetonitrile (111 uL, 0.46 mmol) in acetonitrile (10 mL). After stirring at room temperature in the dark for 18 h, the mixture was filtered, then concentrated. The title compound was obtained in 60% yield by preparative TLC using 25% ethyl acetate in petroleum ether as eluent.

$^1$HNMR: consistent with structure.

HPLC: method A, Rt=12.21 min; 97%

TLC: R$_f$=0.2 (20% ethyl acetate in petroleum ether)

Analysis calculated for C$_{36}$H$_{45}$N$_3$O$_4$S+0.45 water C, 69.30; H, 7.42; N, 6.73 Found: C, 69.34; H, 7.39; N, 7.02

EXAMPLE 32

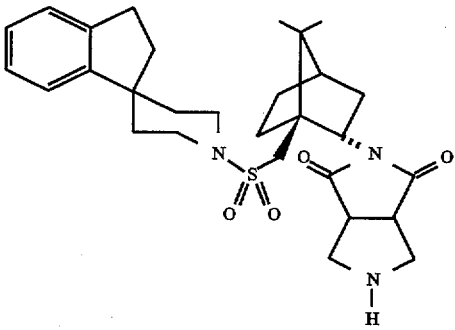

To a solution of the product of Example 31 (50 mg, 0.081 mmol) in ethanol (15 mL) was added palladium black (5 mg), followed by acetic acid (1 drop). After stirring at room temperature under an atmosphere of hydrogen for 18 h, the mixture was filtered then concentrated. The title compound was obtained by preparative HPLC (20 mg).

$^1$HNMR: consistent with structure.

HPLC: method A, R$_t$=11.97 min; 97%

TLC: R$_f$=0.5 (10% methanol in methylene chloride)

Analysis calculated for C$_{29}$H$_{39}$N$_3$O$_4$S+1.25 trifluoroacetic acid+0.60 toluene. C, 59.26; H, 6.28; N, 5.81 Found: C, 59.27; H, 6.26; N, 5.86

EXAMPLE 33

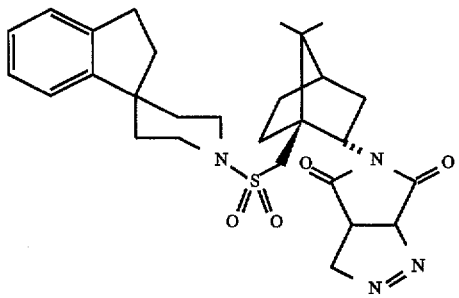

To a solution of the product of Example 29 (660 mg, 1.37 mmol) in 1:1 tetrahydrofuran:diethyl ether (200 mL) was added an ethereal solution of diazomethane (approximately 5 eq.). After stirring at room temperature for 1 h, acetic acid (2 drops) was added, then the mixture was concentrated. The title compound (717 mg) was obtained as a 3:1 mixture of diastereomers by flash chromatography using 40% ethyl acetate in petroleum ether as eluent.

$^1$HNMR: consistent with structure.

HPLC: method A, Rt=13.48 min (major isomer)

TLC: $R_f$=0.5 (40% ethyl acetate in petroleum ether)

FABMS: M+1 at 525

Analysis calculated for $C_{28}H_{36}N_4O_4S$+0.3 ethyl acetate C, 63.93; H, 7.02; N, 10.17 Found: C, 63.94; H, 7.09; N, 10.13

EXAMPLE 34

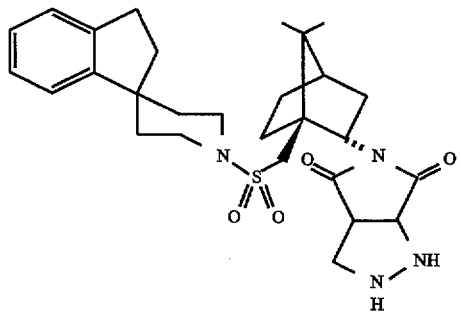

To a solution of the product of Example 33 (40 mg, 0.08 mmol) in 9:1 methanol:acetic acid (20 mL) was added zinc dust (10 eq). After stirring at room temperature for 4 h, the mixture was filtered and concentrated. The title compound (15 mg) was obtained through purification by flash chromatography (10% methanol in methylene chloride as eluent).

$^1$HNMR: consistent with structure.

HPLC: method A, $R_t$=11.03

FABMS: M+1 at 527

Analysis calculated for $C_{28}H_{38}N_4O_4S$+0.5 water+0.25 hexanes C, 63.59; H, 7.69; N, 10.05 Found: C, 63.61; H, 7.31; N, 9.79

EXAMPLE 35

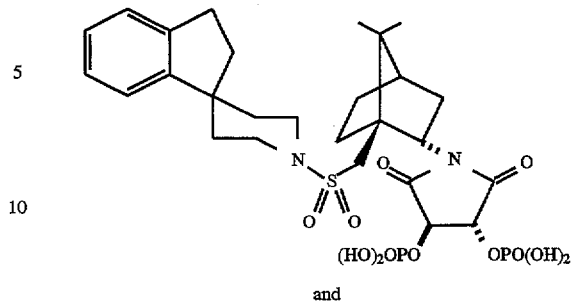

and

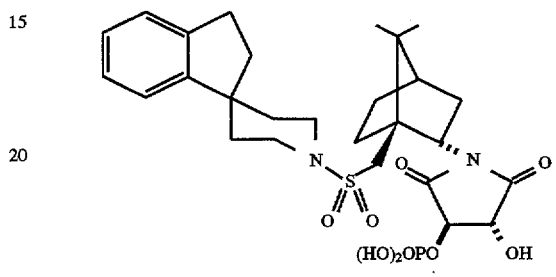

To a solution of the product of Example 23 (1.03 g, 2 mmol) in dry tetrahydrofuran(100 mL) was added diethylamino dibenzylphosphoramidite (1.78 g, 04 mmol), followed by tetrazole (280 mg, 4 mmol). After 2 h, the solution was cooled to −40° C., then m-chloroperbenzoic acid (1 g, 4 mmol) in methylene chloride (12 mL) was added dropwise. The solution was allowed to warm to 5° C. After 18 h, the mixture was partitioned between aqueous sodium bisulfite and methylene chloride. The methylene chloride layer was dried over sodium sulfate, then concentrated. Flash chromatography (3% methanol in methylene chloride as eluent) allowed the separation of two phosphorylated intermediates (mono and diphosphorylated adducts) which were hydrogenated separately.

Each of the two phosphorylated intermediates was dissolved in ethanol. Palladium on carbon (10%) was added, then the mixtures were placed under hydrogen atmosphere. After 18 h, the mixtures were filtered and concentrated. The product phosphates were purified by preparative HPLC.

mono phosphate:

$^1$HNMR: consistent with structure.

HPLC: method B, $R_t$=11.27 min.

FABMS: M+1 at 597

Analysis calculated for $C_{27}H_{37}N_2O_9S_1P_1$+0.65 trifluoroacetic acid+0.70 dioxane C, 51.00; H, 5.95; N, 3.83 Found: C, 51.05; H, 6.35; N, 4.21 di phosphate:

$^1$HNMR: consistent with structure.

HPLC: $R_t$=10.5 min.

FABMS: M+1 at 677

Analysis calculated for $C_{27}H_{38}N_2O_{12}P_2S_1$+1.50 dioxane C, 49.00; H, 6.23; N, 3.46 Found: C, 48.97; H, 6.24; N, 3.43

EXAMPLE 36

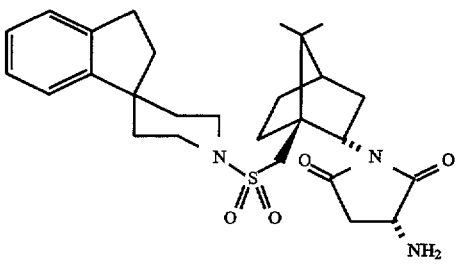

To a solution of endo-[1S]-1'[[[2-amino-7,7-dimethylbicyclo[2.2.1]-hept-1yl]-methyl]-sulfonyl]spiro[1H-indan-1-4'-piperidine](4 g, 0.01 mol) in methylene chloride (20 mL) was added Boc-(D)-Aspartic acid beta-benzyl ester (3.32 g, 0.012 mol), hydroxybenzotriazole (1.62 g, 0.012 mol), and 1-(3-dimethylaminopropyl)-3-ethylcarbodiimide hydrochloride (2.3 g, 0.012 mmol). After 18 hours the solution was concentrated, then partitioned between ethyl acetate and 1M NaOH (150 mL each). The organic layer was washed with 1M HCl, and brine (150 mL each) then dried over $Na_2SO_4$. The solution was filtered then concentrated. Purification by flash chromatography (40% ethyl acetate in petroleum ether as eluent) gave an amide ester intermediate as white foam (3.7 g).

The foam (2.12 g, 0.003 mol) was dissolved in dry tetrahydrofuran (25 mL) under nitrogen atmosphere, then cooled to −78° C. Lithium hexamethyldisilylazide (7 mL, 1M solution in tetrahydrofuran) was added dropwise. After 4 hours, a saturated solution of ammonium chloride was added, and the reaction mixture was allowed to warm to room temperature. The mixture was partitioned between ethyl acetate and water (150 mL each). The ethyl acetate layer was dried 3.0 over sodium sulfate, then concentrated. Purification by flash chromatography (gradient from 15% to 20% ethyl acetate in petroleum ether as eluent) afforded a protected aminosuccinimide intermediate as a white foam.

To a solution of the Boc protected aminosuccinimide (2.7 g) in methylene chloride (10 mL) was added trifluoroacetic acid (5 mL). After 3 h, the mixture was concentrated. Purification by flash chromatography (3% methanol in methylene chloride as eluent) afforded the title compound as a white foam (1.6 g).

$^1$HNMR: consistent with structure.

HPLC: method B, $R_t$=11.96 min.

FABMS: M+1 at 500

Analysis calculated for $C_{27}H_{37}N_3O_4S_1$+0.25 methylene chloride

C, 62.83; H, 7.26; N, 8.07 Found: C, 62.81; H, 7.19; N, 8.08

EXAMPLE 37

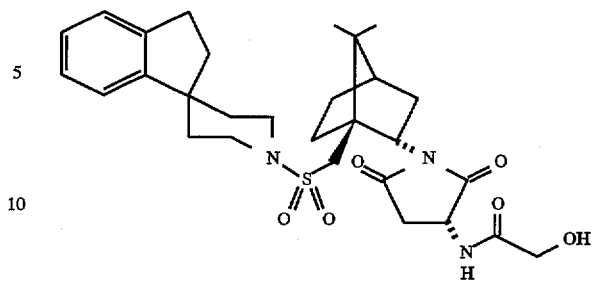

To a solution of the product of Example 36 (24 mg, 0.05 mmol) in acetonitrile (1 mL) was added glycolic acid (9 mg, 0.06 mmol), followed by benzotriazolyl-N-oxy-tris (dimethylamino)phosonium hexafluorophosphate (26 mg, 0.06 mmol) and diisopropylethylamine (7.8 mg, 0.06 mmol). After 18 h, the mixture was concentrated. The title compound was obtained after purification by preparative HPLC (17 mg).

$^1$HNMR: consistent with structure.

HPLC: method B, $R_t$=14.46 min.

FABMS: M+1 at 558

Analysis calculated for $C_{29}H_{39}N_3O_6S_1$+0.45 trifluoroacetic acid C, 58.96; H, 6.53; N, 6.90 Found: C, 59.06; H, 6.72; N, 6.65

EXAMPLE 38

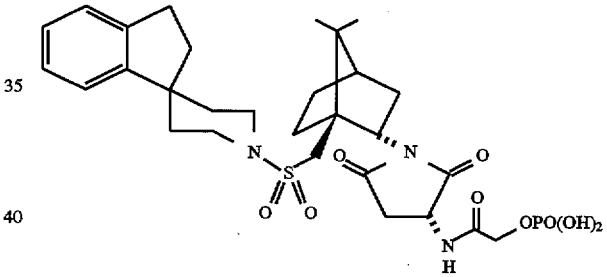

To a solution of the product of Example 37 (200 mg, 0.36 mmol) in dry tetrahydrofuran (15 mL) was added diethylamino dibenzylphosphoramidite (171 mg, 0.54 mmol), followed by tetrazole (75 mg, 1.08 mmol). After 18 h at 9° C., the solution was cooled to −50° C., then m-chloroperbenzoic acid (139 mg) was added and the mixture was allowed to warm to room temperature. After 6 h, the mixture was concentrated, then partitioned between ethyl acetate and aqueous sodium bisulfite. The ethyl acetate was dried over sodium sulfate, then concentrated. Preparative HPLC afforded the intermediate phosphorylated adduct.

The protected phosphate ester obtained above (100 mg) was dissolved in ethanol (10 mL). To this solution was added 10% palladium on carbon (39 mg), then the mixture was placed under a hydrogen atmosphere at 60 psi. After 18 h, the mixture was filtered then concentrated. Preparative HPLC afforded the title compound.

$^1$HNMR: consistent with structure.

HPLC: method B, $R_t$=11.98 min.

FABMS: M+1 at 638

Analysis calculated for $C_{29}H_{40}N_3O_9P_1S_1$+1.5 water+0.6 dioxane C, 52.55; H, 6.71; N, 5.86 Found: C, 52.53; H, 6.42; N, 5.84

EXAMPLE 39

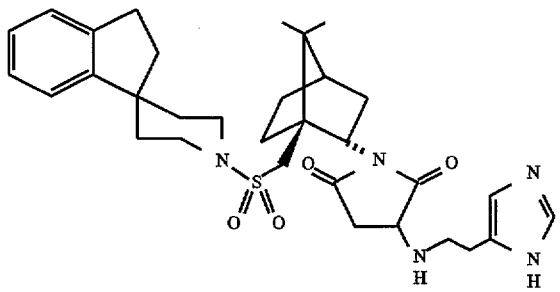

To a solution of the product of Example 29 (24 mg, 0.05 mmol) in methylene chloride (0.5 mL) was added methanol (0.5 mL), followed by histamine dihydrochloride (18 mg, 0.1 mmol) and diisopropylethylamine (26 mg, 0.2 mmol). After 18 h at room temperature the mixture was concentrated. The title compound was purified by preparative HPLC.

$^1$HNMR: consistent with structure.
HPLC: method B, $R_t$=11.05 min.
FABMS: M+1 at 594
Analysis calculated for $C_{32}H_{43}N_5O_4S_1$+2.40 trifluoroacetic acid C, 50.96; H, 5.28; N, 8.07 Found: C, 50.92; H, 5.45; N, 8.14

EXAMPLE 40

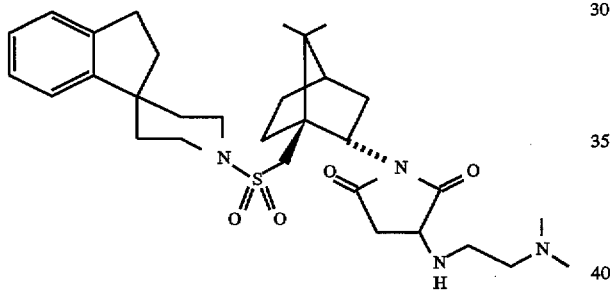

To a solution of the product of Example 29 (48 mg, 0.1 mmol) in methylene chloride (2 mL) was added methanol (2 mL), followed by dimethylaminoethylamine (18 mg, 0.2 mmol). After 18 h at room temperature the mixture was concentrated. The title compound was purified by preparative HPLC.

$^1$HNMR: consistent with structure.
HPLC: method B, $R_t$=12.64 min.
FABMS: M+1 at 571

Analysis calculated for $C_{31}H_{46}N_4O_4S_1$+0.55 water C, 64.11; H, 8.18; N, 9.65 Found: C, 64.07; H, 8.08; N, 9.49

EXAMPLE 41

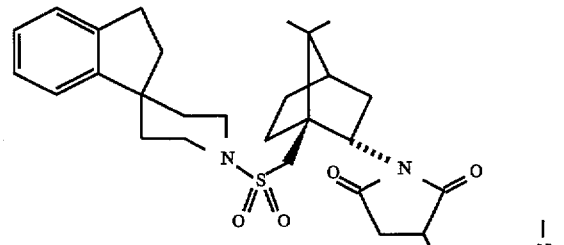

To a solution of the product of Example 29 (48 mg, 0.1 mmol) in methylene chloride (0.5 mL) was added methanol (0.5 mL), followed by dimethylaminoethyl mercaptan hydrochloride (28 mg, 0.2 mmol) and diisopropylethylamine (26 mg, 0.2 mmol). After 18 h at room temperature the mixture was concentrated. The title compound was purified by preparative HPLC.

$^1$HNMR: consistent with structure.

HPLC: method B, $R_t$=13.82 min.

FABMS: M+1 at 588

Analysis calculated for $C_{31}H_{45}N_3O_4S_2$+1.3 TFA+0.05 dioxane C, 54.82; H, 6.36; N, 5.68 Found: C, 54.76; H, 6.37; N, 5.84

EXAMPLE 42

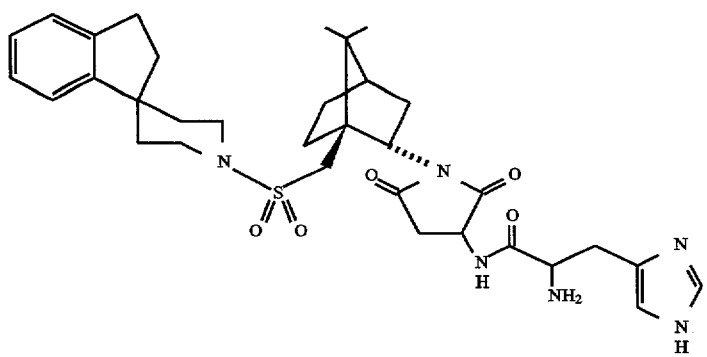

To a solution of the product of Example 36 (25 mg, 0.05 mmol) in acetonitrile (5 mL) was added N-alpha-N-im-bis- Boc-L-Histidine (21 mg, 0.06 mmol), followed by BOP reagent (26 mg, 0.06 mmol) and diisopropylethylamine (7.8 mg, 0.06 mmol). After 18 h at room temperature the mixture was concentrated. Preparative HPLC afforded the Boc protected intermediate, which was dissolved in TFA (5 mL). After 2.5 h, the mixture was concentrated. The title compound was purified by preparative HPLC.

$^1$HNMR: consistent with structure.

HPLC: method B, $R_t$=10.00 min.

FABMS: M+1 at 637

Analysis calculated for $C_{33}H_{44}N_6O_5S_1$+2.20 TFA+1.75 water C, 48.87; H, 5.45; N, 9.14 Found: C, 48.86; H, 5.47; N, 8.96

EXAMPLE 43

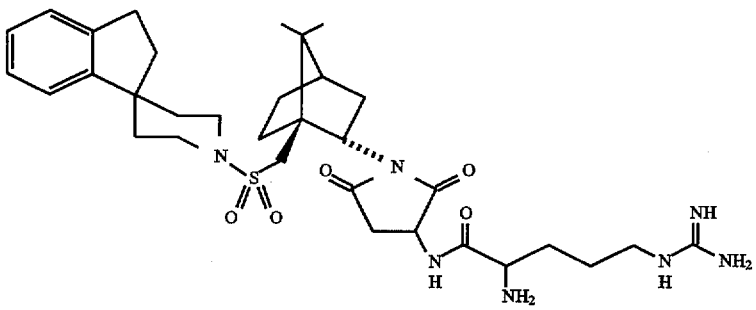

To a solution of the product of Example 36 (100 mg, 0.2 mmol) in DMF (10 mL) was added N-alpha-Boc-L-arginine hydrochloride (75 mg, 0.24 mmol), followed by hydroxybenzotriazole (35 mg, 0.24 mmol), and 1-(3-dimethylaminopropyl)-3-ethylcarbodiimide hydrochloride (50 mg, 0.24 mmol). After 18 h at room temperature the mixture was concentrated. Preparative HPLC afforded the Boc protected intermediate, which was dissolved in 50% TFA in methylene chloride (6 mL). After 18 h, the mixture was concentrated. The title compound (67 mg) was purified by preparative HPLC.

$^1$HNMR: consistent with structure.

HPLC: method B, $R^t$=9.80 min.

FABMS: M+1 at 656

Analysis calculated for $C_{33}H_{49}N_5O_5S_1$+2.5 TFA+1.45 water C, 47.19; H, 5.67; N, 10.14 Found: C, 47.19; H, 5.62; N, 10.13

EXAMPLE 44

To a solution of the product of Example 43 (approx. 0.4 mmol) in methylene chloride (5 mL) was added diisopropylethylamine until the pH was approximately 8.5. Acetyl chloride (31 mg) was added. After 18 h at room temperature the mixture was concentrated. The title compound (138 mg) was purified by preparative HPLC.

$^1$HNMR: consistent with structure.

HPLC: method B, $R_t$=11.99 min.

FABMS: M+1 at 698

Analysis calculated for C35H51 N7O6S1+1.7 TFA+0.1 dioxane C, 51.74; H, 5.99; N, 10.89 Found: C, 51.72; H, 6.13; N, 11.01

EXAMPLE 45

1-((7,7-Dimethyl-2-Oximino-Bicyclo(2.2.1)Heptan-1-yl)-Methane-sulfonyl)-4-(2-Methylphenyl)-3-Piperazine

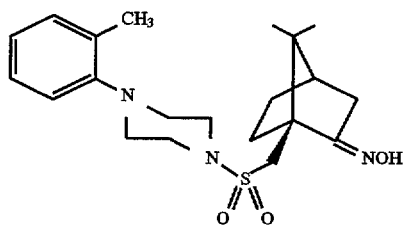

To a stirred solution of 1-((7,7-dimethyl-2-oxo-bicyclo-(2.2.1)heptan-1-yl)methanesulfonyl)-4-(2-methylphenyl) piperazine (65.0 g; 166 mmol) in pyridine (250 mL) was added hydroxylamine hydrochloride (35.0 g; 0.504 mol). The solution was heated to 70° C. for 18 h. The solvent was removed under reduced pressure, the residue was taken up in chloroform (500 mL) and washed with aqueous NaHCO$_3$ (2×200 mL), water (100 mL), and 5% aqueous HCl (2×200 mL). The organic phase was dried (MgSO$_4$), filtered, and the solvent was removed under reduced pressure. The title

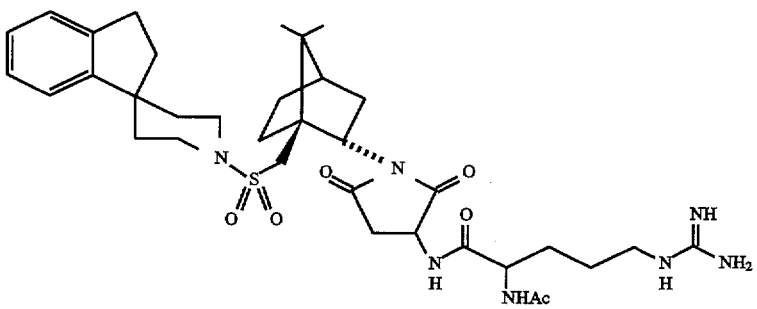

compound crystallized from ethyl acetate, giving off-white needles (57 g; 84%), mp 174°–175° C.

TLC: R$_f$0.40 (7525 hexane-ethyl acetate)

HPLC (method A): retention time 9.98 min

FABMS: M+1 at 406

Analysis calculated for C$_{21}$H$_{31}$N$_3$O$_3$S C, 62.19; H, 7.71; N, 10.36 Found: C, 62.29; H, 7.63; N, 10.15

$^1$H NMR (300 MHz, CDCl$_3$): δ7.90 (br s, 1H), 7.18 (m, 2H), 7.02 (m, 2H), 3.47 (m, 4H), 4.43 (d, J=14.4 Hz, 1H), 3.00 (m, 4H), 2.92 (d, J=14.4 Hz, 1H), 2.4–2.6 (m, 2H), 2.31 (s, 3H), 2.09 (d, J=16.9 Hz, 1H), 1.95 (m, 2H), 1.80 (m, 1H), 1.32 (m, 1H), 1.08 (s, 3H), 0.87 (s, 3H)

EXAMPLE 46

1-((7,7-Dimethyl-2-Endo-Amino-Bicyclo(2.2.1)Heptan-1-yl)Methane-sulfonyl)-4-(2-Methylphenyl)-3-Piperazine

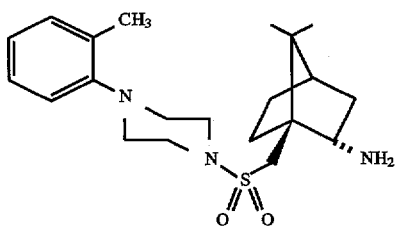

To a stirred solution of 1-((7,7-dimethyl-2-oximino-bicyclo(2.2.1)heptan-1-yl)methanesulfonyl)-4-(2-methylphenyl)piperazine (35.0 g; 86 mmol) in 2-methoxyethanol (500 mL) containing Raney Nickel alloy (105.0 g) was added sodium hydroxide solution (17.2 g; 430 mmol dissolved in 75 mL) dropwise over 30 min. During the addition heat and gas was evolved. The mixture was stirred at ambient temperature for 16 h, at which time TLC indicated complete consumption of starting oxime and a ca. 4:1 mixture of endo (lower R$_f$) and exo (higher R$_f$) amine products. The mixture was filtered through Celite and the filtercake was washed with methanol and ethyl acetate. The solvents were removed under reduced pressure and the resulting solid was dispersed in water and filtered. The dried solid was purified by pressurized silica gel column chromatography, using a 93:3 to 94:6 A:B gradient elution (A=chloroform, B=5% NH$_4$OH/MeOH). The title compound was obtained as a white foam (24 g; 70%).

EXAMPLE 47

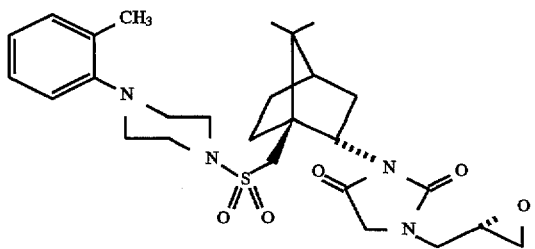

The procedure of example 2 was carried out using the product of example 46 [1.38 mmol], triethylamine [3.40 mmol], and substituting glycine methyl ester hydrochloride [1.54 mmol] for histidine methyl ester dihydrochloride. The intermediate hydantoin was purified by flash chromatography using 5% methanol in methylene chloride as eluent.

To a stirred solution of the hydantoin (120 mg, 0.253 mmol) in dry tetrahydrofuran (15 mL) was added 2R-(−)-glycidyl tosylate (288 mg, 1.26 mmol), followed by sodium hydride (60% dispersion in oil). The temperature was increased to reflux. After 2 hours the mixture was cooled then concentrated. Purification by preparative TLC (40% ethyl acetate in petroleum ether as eluent) afforded [1R-[[4-(2-methylphenyl)piperazin-1-yl)sulfonyl]-methyl]7,7-dimethylbicyclo[2.2.1]hept-2-endo-yl]-3-[2S,3 oxirane-1-propenyl]-2,5-dioxo-1-imidazolidine as a white foam (112 mg).

$^1$HNMR: consistent with structure.

HPLC: method A; R$_f$=13.4 min; 98%

Analysis calculated for C$_{27}$H$_{38}$N$_4$O$_5$S+0.25 methylene chloride C, 59.30; H, 7.03; N, 10.15 Found: C, 59.64; H, 7.10; N, 9.79

EXAMPLE 48

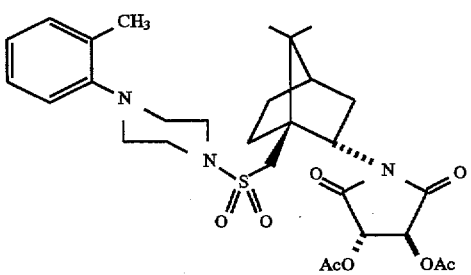

To a solution of 1-((7,7-dimethyl-2-endo-amino-bicyclo-(2.2.1)heptan-1-yl)methanesulfonyl)-4-(2-methylphenyl)-3-piperazine (103 mg, 0.286 mmol) in methylene chloride (15 mL) was added diacetyl tartaric anhydride (71 mg, 0.315 mmol). After stirring for 1 h at room temperature, the mixture was concentrated, then dissolved in acetic anhydride (20 mL). Sodium acetate (47 mg, 0.572 mmol) was added, then the mixture was heated to 70° C. After 40 h, the mixture was cooled to room temperature, then concentrated. Flash chromatography using 20% ethyl acetate in petroleum ether as eluent afforded 61 mg of the title compound as a white foam.

$^1$HNMR: consistent with structure.

HPLC: method A; R$_f$=14.16 min; 98%

FABMS: M+1 at 590

Analysis calculated for C$_{29}$H$_{39}$N$_3$O$_8$S+0.15 hexanes+ 1.15 ethyl acetate C, 58.71; H, 7.15; N, 6.01 Found: C, 58.71; H, 6.91; N, 5.98

EXAMPLE 49

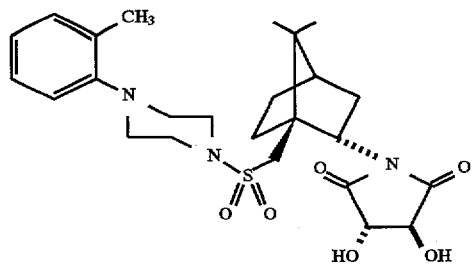

To a solution of the product of Example 48 (20 mg, 0.033 mmol) in 3:1 tetrahydrofuran:water (10 mL) at 0° C. was added hydrogen peroxide (4 eq), followed by lithium hydroxide (2 eq). After stirring at room temperature for 40 min, the mixture was concentrated. Flash chromatography using 10% methanol in methylene chloride as eluent afforded 14 mg of the title compound as a white foam.

¹HNMR: consistent with structure.

HPLC: method A; $R_f$=11.4 min; 97%

FABMS: M+1 at 506

Analysis calculated for $C_{25}H_{35}N_3O_6S$+0.25 chloroform+ 0.20 water C, 56.26; H, 6.67; N, 7.79 Found: C, 56.27; H, 6.55; N, 7.53

EXAMPLE 50

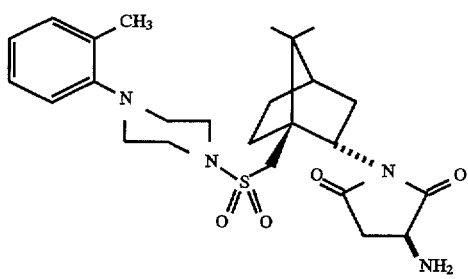

The procedure of Example 36 was followed, where the product of example 46 was used in place of endo-[1S]-1'[[ [2-amino-7,7-dimethylbicyclo[2.2.1]-hept-1yl]-methyl]-sulfonyl]spiro[1H-indan-1-4'-piperidine], and Boc-(L)-Aspartic acid beta-methyl ester was used instead of Boc-(D)-Aspartic acid beta-benzyl ester.

¹HNMR: consistent with structure.

HPLC: method A; $R_f$=10.82 min; 98%

Analysis calculated for $C_{25}H_{36}N_4O_4S$+0.25 hexanes+ 0.50 methylene chloride. C, 58.68; H, 7.39; N, 10.14 Found: C, 58.73; H, 7.23; N, 10.22

EXAMPLE 51

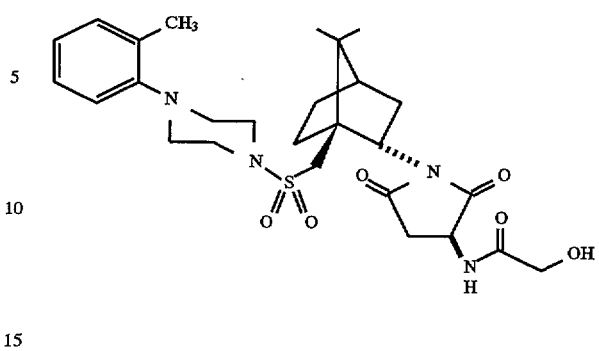

To a solution of the product of Example 50 (50 mg, 0.102 mmol) in methylene chloride (15 mL) was added glycolic acid (12 mg, 0.15 mmol), followed by 1-ethyl-3-(3-dimethylaminopropyl)carbodiimide hydrochloride (29 mg, 0.15 mmol) and 1-hydroxybenzotriazole (21 mg, 0.15 mmol). After stirring at room temperature for 18 h, the mixture was concentrated. The title compound was purified by preparative HPLC.

¹HNMR: consistent with structure.

TLC: $R_f$=0.4 (10% methanol in methylene chloride)

FABMS: M+1 at 547

Analysis calculated for $C_{27}H_{37}N_4O_6S$+0.95 trifluoroacetic acid C, 53.08; H, 5.85; N, 8.57 Found: C, 52.97; H, 6.08; N, 8.17

TABLE

In addition to those compounds specifically exemplified above, additional compounds of the present invention are set forth in tabular form below. These compounds are synthesized by use of the synthetic routes and methods described in the above Schemes and Examples and variations thereof well known to those of ordinary skill in the art, and not requiring undue experimentation. All variables listed in the Tables below are with reference to the following generic structure:

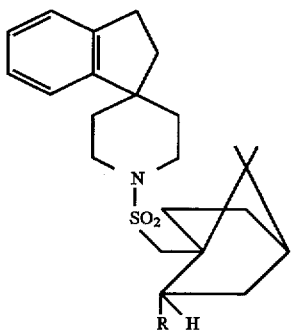

| R | R |
|---|---|
| 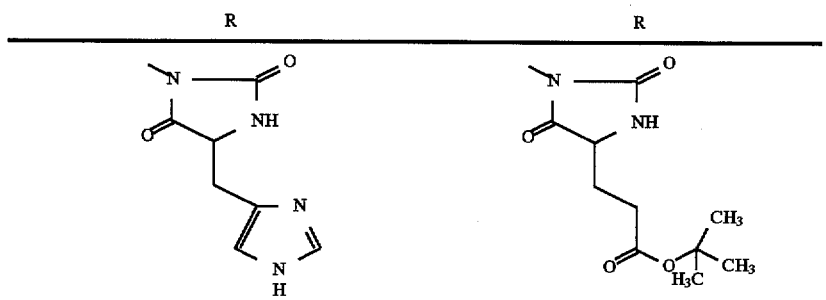 | |

TABLE-continued

In addition to those compounds specifically exemplified above, additional compounds of the present invention are set forth in tabular form below. These compounds are synthesized by use of the synthetic routes and methods described in the above Schemes and Examples and variations thereof well known to those of ordinary skill in the art, and not requiring undue experimentation. All variables listed in the Tables below are with reference to the following generic structure:

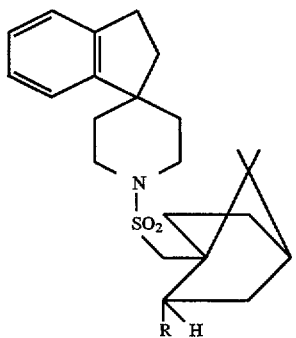

| R | R |
|---|---|
| | 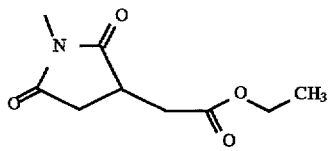 |
| 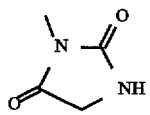 | 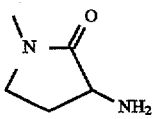 |
| 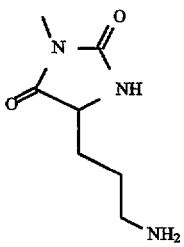 | 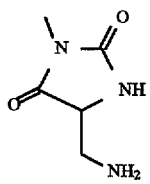 |
| 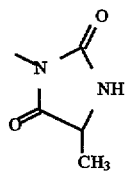 | 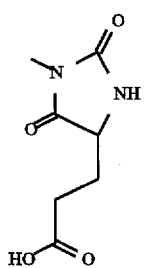 |
| 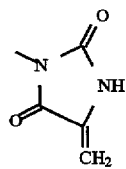 | 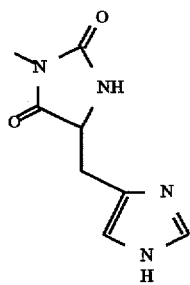 |

TABLE-continued

In addition to those compounds specifically exemplified above, additional compounds of the present invention are set forth in tabular form below. These compounds are synthesized by use of the synthetic routes and methods described in the above Schemes and Examples and variations thereof well known to those of ordinary skill in the art, and not requiring undue experimentation. All variables listed in the Tables below are with reference to the following generic structure:

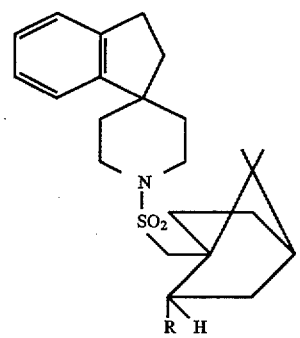

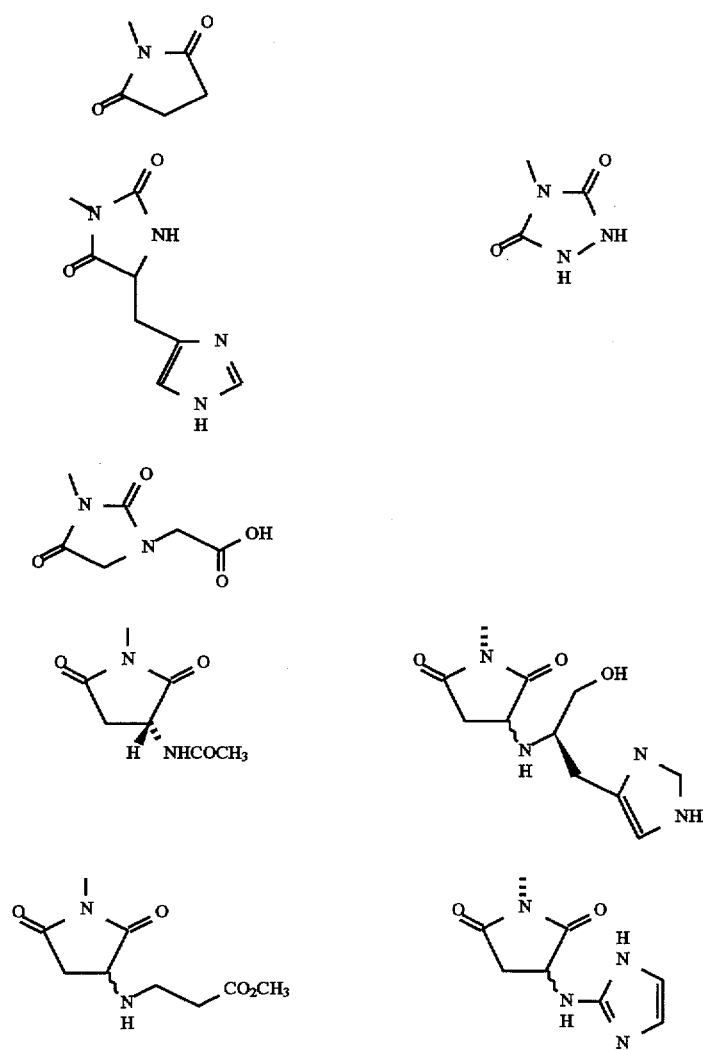

| R | R |
|---|---|

TABLE-continued

In addition to those compounds specifically exemplified above, additional compounds of the present invention are set forth in tabular form below. These compounds are synthesized by use of the synthetic routes and methods described in the above Schemes and Examples and variations thereof well known to those of ordinary skill in the art, and not requiring undue experimentation. All variables listed in the Tables below are with reference to the following generic structure:

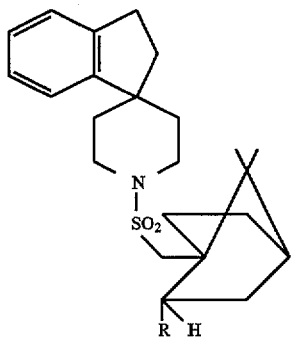

| R | R |
|---|---|
| 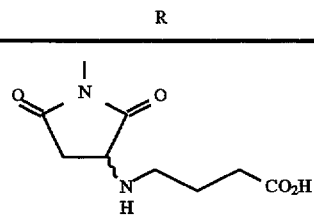 | 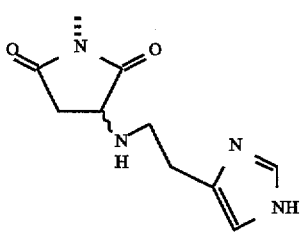 |
| 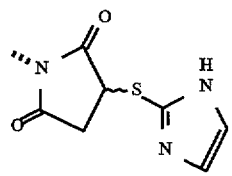 | 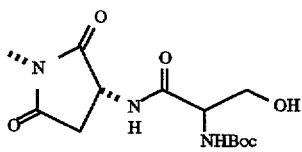 |
| 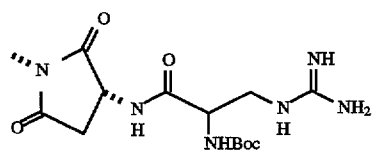 | 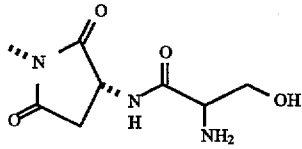 |
| 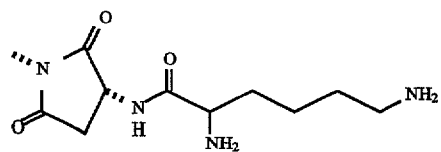 | 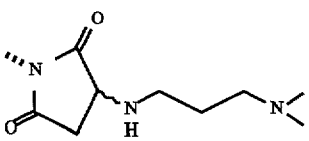 |
| 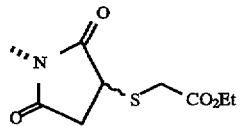 | 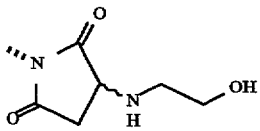 |
| 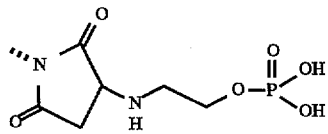 | 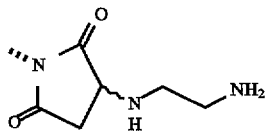 |

TABLE-continued

In addition to those compounds specifically exemplified above, additional compounds of the present invention are set forth in tabular form below. These compounds are synthesized by use of the synthetic routes and methods described in the above Schemes and Examples and variations thereof well known to those of ordinary skill in the art, and not requiring undue experimentation. All variables listed in the Tables below are with reference to the following generic structure:

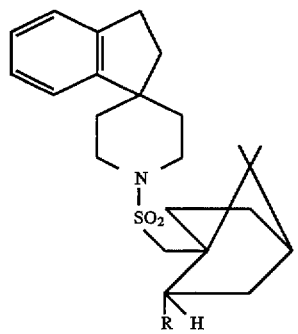

TABLE-continued

In addition to those compounds specifically exemplified above, additional compounds of the present invention are set forth in tabular form below. These compounds are synthesized by use of the synthetic routes and methods described in the above Schemes and Examples and variations thereof well known to those of ordinary skill in the art, and not requiring undue experimentation. All variables listed in the Tables below are with reference to the following generic structure:

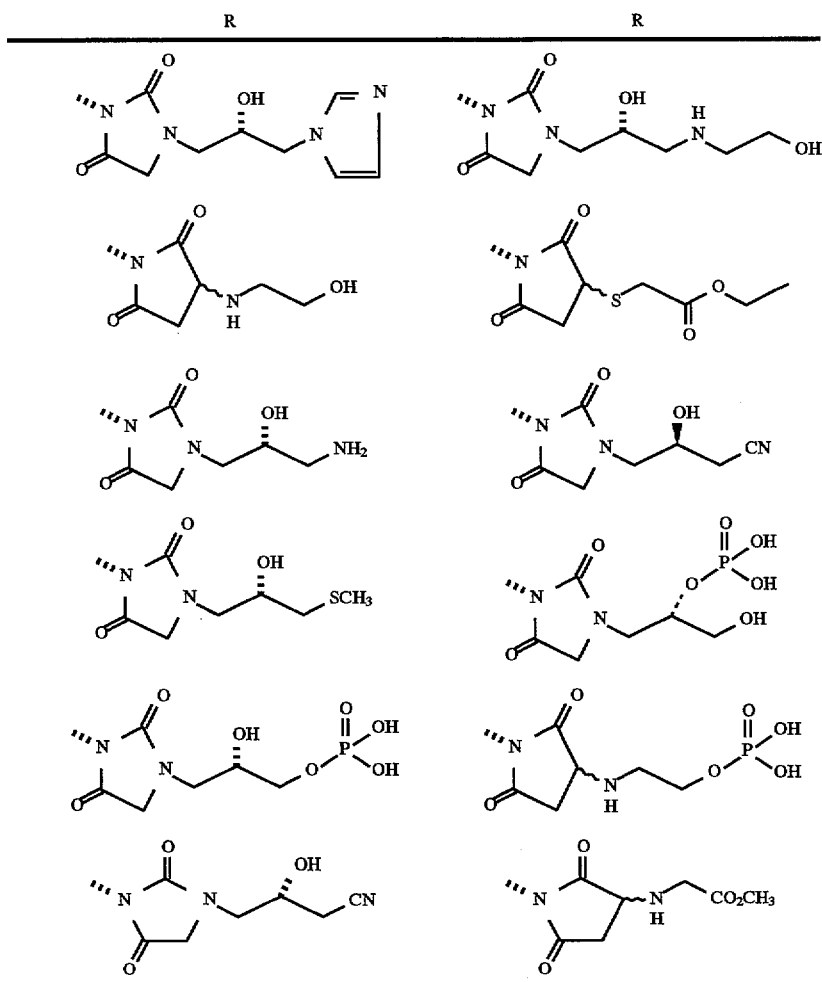

EXAMPLE 52

RADIOLIGAND BINDING ASSAYS

The high affinity binding of [$^3$H] Oxytocin (OT)([tyrosyl, 3,5-[3H]OT; 30–60 Ci/mmol; New England Nuclear. Boston, Mass.) to uterine OT receptors was based on an assay (Fuchs, A.-R; Fuchs, F.; Soloff, M. S. 1985 J. Clin. Endocrinol. Metab. 6037) using a crude membrane preparation of uteri taken from diethylstilbestrol dipropionate (DES)-treated (0.3 mg/kg, ip; 18–24) rats. Competition studies were conducted at equilibrium (60 minutes; 22° C.) using 1 nM[$^3$H]OT in the following assay buffer 50 mM Tris-HCl, 5 mM MgCl$_2$, and 0.1% BSA, pH 7.4. Nonspecific binding (10% of the total binding) was determined using 1

μM unlabeled OT and the binding reaction was terminated by filtration through glass fiber filters using a cell harvester (model 7019, Skatron, Inc., Sterling, Va.). $IC_{50}$ (the concentration of tested compound that inhibits 50% of OT) was reported, unless otherwise noted.

The measurement of [$^3$H]Vasopressin (AVP) ([phenylalanyl-3,4,5-$^3$H]AVP; 80–90 Ci/mmol; New England Nuclear) binding to a crude membrane preparation of male rat liver (AVP-V 1 sites) or kidney medulla (AVP-V2 sites) was determined according to the method of Butlen, et al. (Butlen, D; Guillon, G; Rajerison, R. M.; Jard, S; Sawyer, W. H.; Manning, M. 1978 Mol Pharmacol 14:1006).

Competition assays were conducted at equilibrium (30 minutes at 30° C.) using 1 nM [$^3$H]AVP (liver) or 2 nM [$^3$H]AVP (kidney) in the following assay buffer 100 mM Tris-HCl, 5 mM $MgCl_2$, 0.1% BSA, 50 mM phenylmethylsulfonylfluoride, and 50 mg/ml bacitracin, pH 8.0. Nonspecific binding (5–10% of the total binding) was determined using 10 μM unlabeled AVP, and the binding reaction was terminated by filtration as described above for the [$^3$H]OT binding assay.

$IC_{50}$ values were determined for both [$^3$H]OT and [$^3$H] AVP binding assays by linear regression of the relation log concentration of compound vs. percent inhibition of specific binding.

| Example | Result For [$^3$H]OT |
|---|---|
| 29 | 70% inhib. @1000 nM |
| 32 | 29 nM |
| 38 | 4.9 nM |
| 44 | 1.0 nM |
| 48 | 67 nM |
| 49 | 68 nM |

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth hereinabove may be applicable as a consequence of variations in the responsiveness of the mammal being treated for prevention of preterm labor, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula

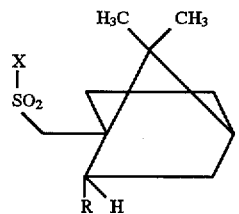

or a pharmaceutically acceptable salt thereof, wherein X is

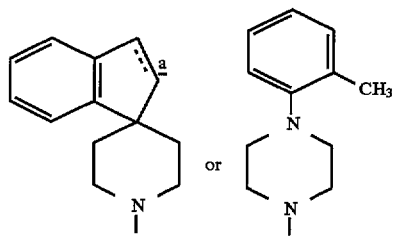

a is a single or double bond,

R is Het, wherein

Het is a substituted saturated or unsaturated heterocyclic ring wherein said substituents are independently one or more of $R^1$, $R^2$, $R^3$, Alk-$R^1$, Alk-$R^2$, Alk-$R^3$, —NHC(O)-Alk-$R^2R^3$, —N$R^5$-Alk-$R^2R^3$ or Alk-$R^2R^3$; where Alk is $C_{1-10}$ alkyl and $R^1$, $R^2$ and $R^3$ are independently selected from the group consisting of hydrogen, halogen, $C_{2-10}$ alkenyl, methylene, $C_{1-10}$ alkoxycarbonyl, $C_{1-10}$ alkoxycarbonyl-$C_{1-10}$ alkylamino, $C_{1-10}$ alkoxycarbonylamino, $C_{1-10}$ alkylamino-$C_{1-10}$ alkylaminocarbonyl, $C_{1-10}$ alkylcarbonylamino, —S—$R^4$, $C_{1-10}$ alkylcarbonyloxy, $C_{1-10}$ alkylsulfonyl, $C_{1-10}$ alkylthio, amino, amino $C_{1-10}$ alkylcarbonylamino, amino $C_{1-10}$ alkylamino, carbonylamino, carbamoyl, carboxyl $C_{1-10}$ alkylamino, carboxyl, cyano, di-$C_{1-10}$ alkylamino, di-$C_{1-10}$ alkylamino-$C_{1-10}$ alkylamino, di-$C_{1-10}$ alkylamino-$C_{1-10}$ alkylthio, di-$C_{1-10}$ alkylamino-$C_{1-10}$ alkylaminocarbonyl, guanidinyl, hydroxyl, hydroxyl $C_{1-10}$ alkylamino, imidazolyl, imidazolyl amino, imidazolyl $C_{1-10}$ alkylamino, imidazolyl $C_{1-10}$ alkylaminocarbonyl, morpholinyl, thiomorpholinyl, dioxothiomorpholinyl, indolyl, oxo, oxiranyl, phenyl, piperidinylamino, piperazinyl, pyrrolidinyl, sulfonyl, tetrazolyl $C_{1-10}$ alkyl-carbonylamino, tetrazolylaminocarbonyl, phosphoryl, phosphoryl $C_{1-10}$ alkylamino and thiono;

$R^4$ is selected from the group consisting of imidazolyl, $C_{1-10}$ alkoxycarbonyl-$C_{1-10}$ alkyl, di-$C_{1-10}$ alkylamino-$C_{1-10}$ alkyl and $C_{1-5}$ alkyl; and $R^5$ is selected from the group consisting of hydrogen and $C_{1-5}$ alkyl.

2. The compound as claimed in claim 1, wherein

Het is a mono, di, tri or tetra substituted saturated or unsaturated 5 or 6 membered heterocyclic or 7 to 10 membered heterobicyclic ring containing 1, 2 or 3 nitrogen atoms, and $R^1$, $R^2$ and $R^3$ are independently selected from the group consisting of hydrogen, halogen, $C_{2-10}$ alkenyl, methylene, $C_{1-10}$ alkoxycarbonyl, $C_{1-10}$ alkoxycarbonyl-$C_{1-10}$ alkylamino, $C_{1-10}$ alkylcarbonylamino, $C_{1-10}$ alkylcarbonyloxy, $C_{1-10}$ alkylsulfonyl, —S—$R^4$, amino, amino-$C_{1-10}$ alkylcarbonylamino, amino $C_{1-10}$ alkylamino, carbamoyl, carboxyl $C_{1-10}$ alkylamino, carboxyl, cyano, di-$C_{1-10}$ alkylamino, di-$C_{1-10}$ alkylamino-$C_{1-10}$ alkylamino, di-$C_{1-10}$ alkylamino-$C_{1-10}$ alkylthio, di-$C_{1-10}$ alkylamino-$C_{1-10}$ alkylaminocarbonyl, guanidinyl, hydroxyl, hydroxyl $C_{1-10}$ alkylamino, imidazolyl, imidazolyl amino, imidazolyl $C_{1-10}$ alkylamino, morpholinyl, thiomorpholinyl, dioxothiomorpholinyl, indolyl, oxo, oxiranyl, phenyl, piperidinylamino, piperazinyl, sulfonyl, phosphoryl, phosphoryl $C_{1-10}$ alkylamino and thiono.

3. The compound as claimed in claim 2, wherein said bicyclic ring is bonded to one of said heterocyclic or heterobicyclic ring's nitrogen atoms.

4. The compound as claimed in claim 3, wherein X is,

and $R^1$, $R^2$ and $R^3$ are independently selected from the group consisting of hydrogen, halogen, $C_{2-10}$ alkenyl, $C_{1-10}$ alkoxycarbonyl, $C_{1-10}$ alkoxycarbonyl-$C_{1-10}$ alkylamino, $C_{1-10}$ alkylcarbonylamino, $C_{1-10}$ alkylsulfonyl, —S—$R^4$, amino, amino-$C_{1-10}$ alkylcarbonylamino, amino $C_{1-10}$ alkylamino, carbamoyl, carboxyl, cyano, di-$C_{1-10}$ alkylamino, di-$C_{1-10}$ alkylamino-$C_{1-10}$ alkylamino, di-$C_{1-10}$ alkylamino-$C_{1-10}$ alkylthio, guanidinyl, hydroxyl, hydroxyl $C_{1-10}$ alkylamino, imidazolyl, imidazolyl amino, imidazolyl $C_{1-10}$ alkylamino, morpholinyl, thiomorpholinyl, dioxothiomorpholinyl, indolyl, oxo, phenyl, piperidinylamino, piperazinyl, sulfonyl, phosphoryl, phosphoryl $C_{1-10}$ alkylamino and thiono.

5. The compound as claimed in claim 3, wherein Het is selected from the group consisting of imidazolyl, imidazolinyl, imidazolidinyl, pyrrolyl, dihydropyrrolyl, pyrrolidinyl, piperazinyl, triazaspirodecane, pyrrolo-isoxazole, pyrrolo-pyrazole and pyrrolo-pyrrole.

6. The compound as claimed in claim 1, wherein X is

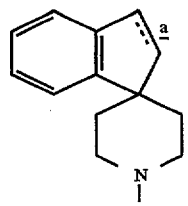

R is Het, wherein

Het is a mono, di, tri or tetra substituted saturated or unsaturated 5 or 6 membered heterocyclic ring containing 1, or 2 nitrogen atoms that is bonded to said bicyclic ring at one of said heterocyclic ring's nitrogen atoms, wherein said substituents are independently one or more of $R^1$, $R^2$, $R^3$, Alk-$R^1$, Alk-$R^2$, Alk-$R^3$ or Alk-$R^2R^3$; and where Alk is $C_{1-10}$ alkyl and $R^1$, $R^2$ and $R^3$ are independently selected from the group consisting of hydrogen, $C_{2-10}$ alkenyl, $C_{1-10}$ alkoxycarbonyl, $C_{1-10}$ alkoxycarbonyl-$C_{1-10}$ alkylamino, $C_{1-10}$ alkoxycarbonylamino, $C_{1-10}$ alkylamino-$C_{1-10}$ alkylaminocarbonyl, $C_{1-10}$ alkylcarbonylamino, $C_{1-10}$ alkylcarbonyloxy, $C_{1-10}$ alkylsulfonyl, $C_{1-10}$ alkylthio, amino, amino-$C_{1-10}$ alkylcarbonylamino, carbonylamino, carboxyl $C_{1-10}$ alkylamino, carboxyl, cyano, di-$C_{1-10}$ alkylamino, di-$C_{1-10}$ alkylamino $C_{1-10}$ alkylaminocarbonyl, guanidinyl, hydroxyl, imidazolyl, imidazolyl $C_{1-10}$ alkylaminocarbonyl, indolyl, oxo, phenyl, piperidinylamino, piperizinyl, pyrrolidinyl, sulfonyl, tetrazolyl $C_{1-10}$ alkylcarbonylamino, tetrazolylaminocarbonyl and thiono.

7. The compound as claimed in claim 6, wherein a is a single bond, and $R^1$, $R^2$ and $R^3$ are independently selected from the group consisting of hydrogen, $C_{2-10}$ alkenyl, $C_{1-10}$ alkoxycarbonyl, $C_{1-10}$ alkoxycarbonyl-$C_{1-10}$ alkylamino, $C_{1-10}$ alkylcarbonylamino, $C_{1-10}$ alkylcarbonyloxy, $C_{1-10}$ alkylsulfonyl, amino, amino-$C_{1-10}$ alkylcarbonylamino, carbonylamino, carboxyl, cyano, di-$C_{1-10}$ alkylamino, di-$C_{1-10}$ alkylamino-$C_{1-10}$ alkylaminocarbonyl, guanidinyl, hydroxyl, imidazolyl, imidazolyl $C_{1-10}$ alkylaminocarbonyl, indolyl, oxo, phenyl, piperidinylamino, piperazinyl, sulfonyl and thiono.

8. The compound as claimed in claim 7, wherein Het is selected from the group consisting of imidazolyl, imidazolinyl, imidazolidinyl, pyrrolyl, dihydropyrrolyl, pyrrolidinyl and piperazinyl.

9. The compound as claimed in claim 2, wherein X is

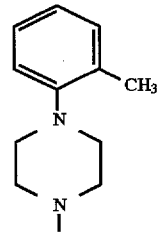

and $R^1$, $R^2$ and $R^3$ are independently selected from the group consisting of hydrogen, halogen, $C_{2-10}$ alkenyl, $C_{1-10}$ alkoxycarbonyl, $C_{1-10}$ alkoxycarbonyl-$C_{1-10}$ alkylamino, $C_{1-10}$ alkylcarbonylamino, $C_{1-10}$ alkylcarbonyloxy, $C_{1-10}$ alkylsulfonyl, —S—$R^4$, amino, amino-$C_{1-10}$ alkylcarbonylamino, amino $C_{1-10}$ alkylamino, carbamoyl, carboxyl, cyano, di-$C_{1-10}$ alkylamino, di-$C_{1-10}$ alkylamino-$C_{1-10}$ alkylamino, di-$C_{1-10}$ alkylamino-$C_{1-10}$ alkylthio, guanidinyl, hydroxyl, hydroxyl $C_{1-10}$ alkylamino, imidazolyl, imidazolyl amino, imidazolyl $C_{1-10}$ alkylamino, morpholinyl, thiomorpholinyl, dioxothiomorpholinyl, indolyl, oxo, oxiranyl, phenyl, piperidinylamino, piperazinyl, sulfonyl, phosphoryl, phosphoryl $C_{1-10}$ alkylamino and thiono.

10. The compound as claimed in claim 9, wherein $R^1$, $R^2$ and $R^3$ are independently selected from the group consisting of hydrogen, $C_{1-10}$ alkylcarbonyloxy, amino, hydroxyl, oxo, phosphoryl and oxiranyl.

11. The compound as claimed in claim 5, selected from the group consisting of

63

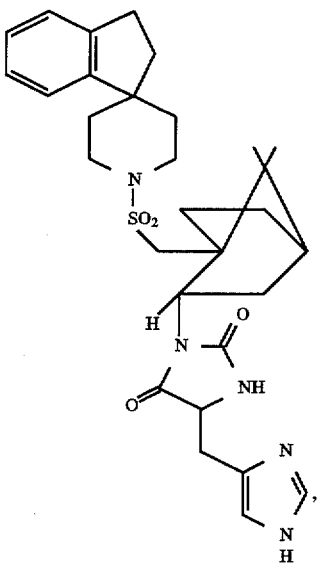

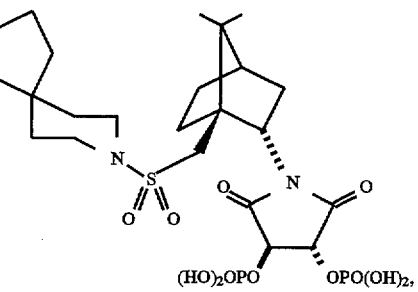

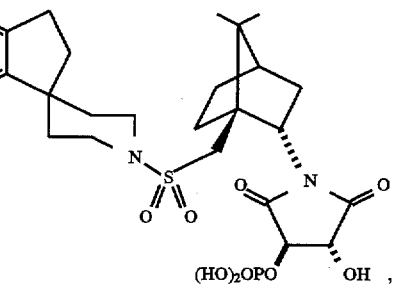

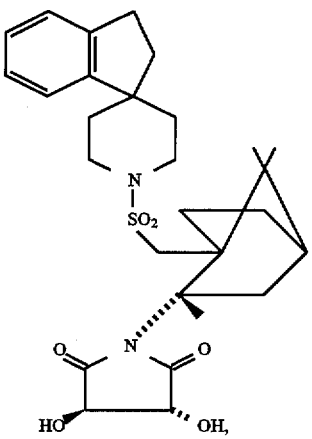

64
-continued

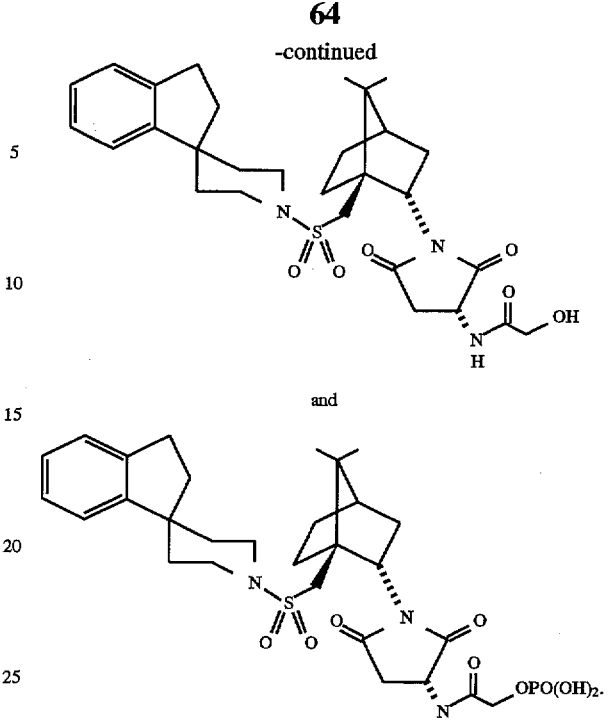

and

12. A pharmaceutical composition comprising a pharmaceutically acceptable carrier and a pharmacologically effective amount of the compound as claimed in claim 1, sufficient to antagonize oxytocin from binding to its receptor site.

13. A pharmaceutical composition comprising a pharmaceutically acceptable carrier and a pharmacologically effective amount of the compound as claimed in claim 1 sufficient to prevent preterm labor in a mammal in need thereof.

14. A pharmaceutical composition comprising a pharmaceutically acceptable carrier and a pharmacologically effective amount of the compound as claimed in claim 1, sufficient to stop labor preparatory to cesarian delivery.

15. A pharmaceutical composition comprising a pharmaceutically acceptable carrier and a pharmacologically effective amount of the compound as claimed in claim 1, sufficient to treat dysmenorrhea.

16. A compound of the formula

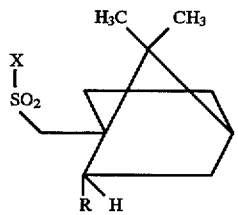

or a pharmaceutically acceptable salt thereof, wherein

X is

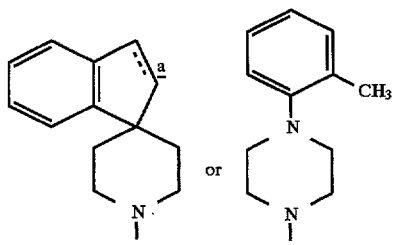

or

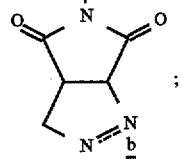

a and b represent a single or double bond,

R is selected from the group consisting of

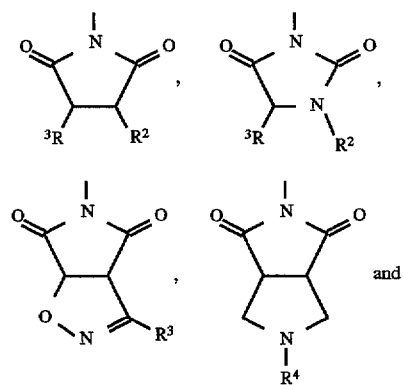

and

-continued

![structure 5]

$R^2$ is selected from the group consisting of -Alk$R^5R^6$, —NH—C(O)-Alk-$R^7R^8$, —N($R^4$)-Alk-$R^7R^8$, amino $C_{1-10}$ alkylcarbonylamino, piperidinylamino, oxiranyl $C_{1-10}$ alkyl, imidazolylamino, $C_{1-10}$ alkoxycarbonyloxy, hydroxyl, phosphoryl, —S—$R^9$, $C_{1-10}$ alkylcarbonyloxy and $C_{1-10}$ alkylcarbonylamino; Alk is $C_{1-10}$ alkyl;

$R^3$ is selected from the group consisting of hydrogen, hydroxyl, phosphoryl, $C_{1-10}$ alkylcarbonyloxy and $C_{1-10}$ alkoxycarbonyl;

$R^4$ is selected from the group consisting of hydrogen, benzyl and $C_{1-10}$ alkyl;

$R^5$ and $R^6$ are independently selected from the group consisting of hydroxyl, di-$C_{1-10}$ alkylamino, piperazinyl, halogen, phosphoryl, morpholinyl, thiomorpholinyl, dioxothiomorpholinyl, hydroxyl $C_{1-10}$ alkylamino, cyano and —SCH$_3$;

$R^7$ and $R^8$ are independently selected from the group consisting of hydrogen, hydroxyl, hydroxyl $C_{1-10}$ alkyl, $C_{1-10}$ alkylcarbonylamino, amino, phosphoryl, imidazolyl, di-$C_{1-10}$ alkylamino, guanidinyl, $C_{1-10}$ alkoxycarbonyl, carboxyl and $C_{1-10}$ alkoxycarbonylamino;

$R^9$ is selected from the group consisting of di-$C_{1-10}$ alkylamino-$C_{1-10}$ alkyl, imidazolyl and $C_{1-10}$ alkoxycarbonyl-$C_{1-10}$ alkyl; provided that $R^5$ and $R^6$ cannot both be hydroxyl.

* * * * *